US008344178B2

(12) United States Patent
Rangachari et al.

(10) Patent No.: US 8,344,178 B2
(45) Date of Patent: Jan. 1, 2013

(54) PROCESSES FOR PRODUCING AND RECOVERING SHIKIMIC ACID

(75) Inventors: Sunder Rangachari, Ballwin, MO (US); Todd C. Friedman, Imperial, MO (US); Greg Hartmann, Kirkwood, MO (US); Robert B. Weisenfeld, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 360 days.

(21) Appl. No.: 12/682,961

(22) PCT Filed: Oct. 16, 2008

(86) PCT No.: PCT/US2008/080189
§ 371 (c)(1),
(2), (4) Date: Jul. 27, 2010

(87) PCT Pub. No.: WO2009/052303
PCT Pub. Date: Apr. 23, 2009

(65) Prior Publication Data
US 2010/0298599 A1 Nov. 25, 2010

Related U.S. Application Data

(60) Provisional application No. 60/999,120, filed on Oct. 16, 2007.

(51) Int. Cl.
C07C 62/30 (2006.01)
(52) U.S. Cl. .................................. 562/508; 562/510
(58) Field of Classification Search .................. None
See application file for complete search history.

(56) References Cited

U.S. PATENT DOCUMENTS

| | | | |
|---|---|---|---|
| 5,120,837 A | 6/1992 | Fotheringham et al. |
| 5,168,056 A | 12/1992 | Frost |
| 5,763,483 A | 6/1998 | Bischofberger et al. |
| 5,776,736 A | 7/1998 | Frost et al. |
| 5,866,601 A | 2/1999 | Lew et al. |
| 5,952,375 A | 9/1999 | Bischofberger et al. |
| 6,316,232 B1 | 11/2001 | Sprenger et al. |
| 6,436,664 B1 | 8/2002 | Iomantas et al. |
| 6,472,169 B1 | 10/2002 | Frost et al. |
| 6,613,552 B1 | 9/2003 | Frost et al. |
| 6,794,164 B2 | 9/2004 | Malmberg et al. |
| 2008/0058210 A1 | 3/2008 | Anderson |

FOREIGN PATENT DOCUMENTS

| | | |
|---|---|---|
| EP | 0418840 A2 | 3/1991 |
| EP | 0976734 A2 | 2/2000 |
| EP | 0759917 B1 | 4/2000 |
| EP | 1092766 A1 | 4/2001 |
| EP | 0763127 B1 | 3/2005 |
| WO | 00/44923 A1 | 8/2000 |
| WO | 02/06203 A1 | 1/2002 |
| WO | 02/29078 A2 | 4/2002 |
| WO | 03/057655 A1 | 7/2003 |
| WO | 2007/035323 A1 | 3/2007 |
| WO | 2008/027570 A2 | 3/2008 |
| WO | 2008128076 A | 10/2008 |

OTHER PUBLICATIONS

Nelms, et al., "Novel mutations in the pheA gene of *Escherichia coli* K-12 which result in highly feedback inhibition-resistant variants of chorismate mutase/prephenate dehydrogenase," Appl. Environ. Microbiol., 58(8): 2592-2598 (1992).
Payne, et al., "Isolation of shikimic acid from star aniseed," Journal Chemical Education, 82(4): 599-600 (Apr. 2005).
Pittard, A.J., "Biosynthesis of the Aromatic Amino Acids," *Escherichia coli* and *Salmonella*: Cellular and Molecular Biology, F. C. Neidhardt, American Society for Microbiology Press, Washington, 368-394 (1987).
Pittard, A.J., "Biosynthesis of the Aromatic Amino Acids," *Escherichia coli* and *Salmonella*: Cellular and Molecular Biology, F. C. Neidhardt, American Society for Microbiology Press, Washington, 458-484 (1996).
Pline, et al., "Tolerance and Accumulation of Shikimic Acid in Response to Glyphosate Applications in Glyphosate-Resistant and Nonglyphosate-Resistant Cotton (*Gossypium hirsutum* L.)," Journal of Agricultural and Food Chemistry, 50: 506-512 (2002).
Polen, et al., "The global gene expression response of *Escherichia coli* to L-phenylalanine," Journal of Biotechnology, 115: 221-237 (2005).
Rao et al., "Studies Directed Towards the Synthesis of Immunosuppressive Agent FK-506: Synthesis of the Entire Top-Half" Tetrahedron Letters, 32(4); 547-550 (Jan. 1991).
Roberts, et al., "Evidence for the shikimate pathway in apicomplexan parasites," Nature, 393: 801-805 (Jun. 1998).
Roberts, et al., "The shikimate pathway and its branches in apicomplexan parasites," J. Infect. Dis. 185(Suppl. 1): S25-S36 (2002).
Rohloff, et al., "Practical total synthesis of the anti-influenza drug GS-4104," J. Org. Chem., 63: 4545-4550 (1998).
Sadaka, et al., "Extraction of shikimic and quinic acids," Chem. Eng. Comm., 173: 91-102 (1999).
Starcevic, et al., "Enzymes of the shikimic acid pathway encoded in the genome of a basal metazoan, *Nematostella vectensis*, have microbial origins," Proc. Natl. Acad. Sci. 105(7): 2533-2537 (2008).
Steinrucken, et al., "The herbicide glyphosate is a potent inhibitor of 5-enolpyruvyl-shikimic acid-3-phosphate synthase," Biochem. Biophys. Res. Commun. 94(4): 1207-1212 (1980).
Steinrucken, et al., "5-enolpyruvylshikimate-3-phosphate synthase of *Klebsiella pneumoniae*. 2. Inhibition by glyphosate [N-(phosphonomethyl)glycine]," Eur. J. Biochem., 143: 351-357 (1984).

(Continued)

Primary Examiner — Yevegeny Valenrod
(74) Attorney, Agent, or Firm — Senniger Powers LLP; James E. Davis

(57) ABSTRACT

The present invention generally relates to processes for producing and recovering cyclitolcarboxylic acids such as shikimic acid and quinic acid. In particular, the present invention is directed to processes for producing shikimic acid that comprise contacting glyphosate and an organism that has the common aromatic biosynthetic pathway. The present invention is also directed to recovery of the shikimic acid product from aqueous process streams utilizing membrane separation techniques.

20 Claims, 8 Drawing Sheets

OTHER PUBLICATIONS

Tan, et al., "Synthesis and preliminary evaluation of a library of polycyclic small molecules for use in chemical genetic assays," J. Am. Chem. Soc., 121: 9073-9087 (1999).

Vogel, et al., "Acetylornithinase of *Escherichia coli*: Partial purification and some properties," J. Biol. Chem., 218: 97-106 (1956).

Wanner, B.R., "Phosphorus Assimilation and Control of the Phosphate Regulon," *Escherichia coli* and *Salmonella*: Cellular and Molecular Biology, F. C. Neidhardt, American Society for Microbiology Press, Washington, 1357-1381 (1996).

White et al., "The Synthesis and Absolute Configuration of Mycosporins. A Novel Application of the Staudinger Reaction" J. Am. Chem. Soc., 111(24): 8970-8972 (1989).

Yeung, et al., "A Short Enantioselective Pathway for the Synthesis of the Anti-Influenza Neuraminidase Inhibitor Oseltamivir from 1,3-Butadiene and Acrylic Acid,", J. Am. Chem. Soc., 128: 6310-6311 (2006).

Abrecht, et al., "The Synthetic Development of the Anti-Influenza Neuraminidase Inhibitor Oseltamivir Phosphate (Tamiflu): A Challenge for Synthesis and Process Research," Chimia, 58(9): 621-629 (2004).

Adachi et al., "High Shikimate Production from Quinate with Two Enzymatic Systems of Acetic Acid Bacteria", Biosci Biotechnol Biochem., 70(10): 2579-2582 (2006).

Amrhein, et al., "Biochemica Basis for Glyphosate-Tolerance in a Bacterium and a Plant Tissue Culture," FEBS Letters, 157(1): 191-196 (Jun. 1983).

Amrhein, et al., "The Site of Inhibition of the Shikimate Pathway by Glyphosate. II. Interference of Glyphosate with Chorismate Formation In Vivo and In Vitro," Plant Physiol. 66: 830-834 (1980).

Anderson, et al., "Analytical method for determination of shikimic acid: Shikimic acid proportional to glyphosate application rates," Commun. Soil. Sci. Plant Anal., 32(17&18): 2831-2840 (2001).

Armstrong, et al., "A 37×103 molecular weight plasmid-encoded protein is required for replication and copy number control in the plasmid pSC101 and its temperature-sensitive derivative pHS1," J. Mol. Biol., 175: 331-347 (1984).

Ausubel et al., "Current Protocols in Molecular Biology", Short Protocols in Molecular Biology, Third Edition: 4-1 to 4-4, John Wiley & Sons, Inc., New York (1995).

Baird, et al., "Introduction of a new broadspectrum postemergence herbicide class with utility of herbaceous perennial weed control," Proc. North Central Weed Control Conference, 26: 64-68 (1971).

Balbas, et al., "Plasmid vector pBR322 and its special-purpose derivatives—a review," Gene, 50: 3-40 (1986).

Bentley, et al., "Plasmid-encoded protein: the principal factor in the "metabolic burden" associated with recombinant bacteria," Biotech. and Bioeng., 35: 668-681 (1990).

Bolivar, et al., "Construction and characterization of new cloning vehicles. II. A multipurpose cloning system," Gene, 2(2): 95-113 (1977).

Bongaerts, et al., "Metabolic engineering for microbial production of aromatic amino acids and derived compounds," Metabolic Engineering, 3: 289-300 (2001).

Bornemann, et al., "*Escherichia coli* chorismate synthase catalyzes the conversion of (6S)-6-fluoro-5-enolpyruvylshikimate-3-phosphate to 6-fluorochorismate. Implications for the enzyme mechanism and the antimicrobial action of (6S)-6-fluoroshikimate," J. Biol. Chem., 270(39): 22811-22815 (1995).

Bradley, et al., "Star role for bacteria in controlling flu epidemic?" Nature Reviews Drug Discovery 4: 945-946 (2005).

Brown, et al., "Twists and turns: A tale of two shikimate-pathway enzymes," Biochem. Soc. Trans., 31: 543-547 (2003).

Buehring, et al., "Shikimic acid accumulation in field-grown corn (*Zea mays*) following stimulated glyphosate drift," Journal of Agricultural and Food Chemistry, 55: 819-824 (2007).

Chandran, et al., "Phosphoenolpyruvate availability and the biosynthesis of shikimic acid," Biotechnol. Prog., 19: 808-814 (2003).

Cleophax et al., "A Stereospecific Converstion of (−)-Methyl Tri-O-benzoylquinate to the Corresponding (−)-Methyl Shikimate," Angewandte Chemie International Edition, 10(9): 652-653 (1971).

Cleophax et al., "No. 558.—Voie d'acces facile aux derives de l'acide shikimique at epi-4-shikimique," Bulletine De La Societe Chimique De France 1973 No. 11: 2992-2995.

Dangschat et al., "Kurze Orginalmitteilungen," Die Naturwissenschaften, 26: 562-563 (1938).

Dangschat et al., "Configurational Relationships Between Naturally Occurring Cyclic Plant Acids and Glucose" Biochim Biophys Acta., 4(1-3): 199-204 (1950).

Davies, et al., "(6S)-6-fluoroshikimic acid, an antibacterial agent acting on the aromatic biosynthetic pathway," Antimicrob. Agents Chemother., 38(2): 403-406 (1994).

Davis, et al., "Aromatic biosynthesis. VII. Accumulation of two derivatives of shikimic acid by bacterial mutants," J. Bacteriol., 66:129-136 (1953).

De Clerq, E., "Strategies in the design of antiviral drugs," Nature Reviews/Drug Discovery, 1: 13-25 (2002).

Dell, et al., "Identification and removal of impediments to biocatalytic synthesis of aromatics from D-glucose: Rate-limiting enzymes in the common aromatic pathway of aromatic amino acid biosynthesis," J. Am. Chem. Soc. 115: 11581-11589 (1993).

Falck et al., "Enantiospecific Synthesis of D-myo-Inositol 1,4,5-Trisphosphate from (−)-Quinic Acid", Journal of Organic Chemistry, 54(25): 5851-5852 (1989).

Farina, et al., "Tamiflu: The Supply Problem," Angew. Chem. Int. Ed., 45: 7330-7334 (2006).

Federspiel, et al., "Industrial synthesis of the key precursor in the synthesis of the anti-influenza drug oseltamivir phosphate (Ro 64-0796/002, GS-4104-02): Ethyl (3R,4S,5S)-4,5-epoxy-3-(1-ethylpropoxy)-cyclohex-1-ene-1-carboxylate," Organic Process Research and Development, 3: 266-274 (1999).

Fischer, et al., "Comparative action of glyphosate as a trigger of energy drain in eubacteria," J. Bacteriol.,168(3): 1147-1154 (1986).

Franz et al. "Methods of Preparing Glyphosate," Glyphosate: A Unique Global Herbicide, American Chemical Society, Chapter 8, 233-262 (1997).

Fukuta, et al., "De novo synthesis of Tamiflu via a catalytic asymmetric ring-opening of meso-aziridines with TMSN3," J. Am. Chem. Soc., 128: 6312-6313 (2006).

Garner, et al., "Biosynthesis of Phenylalanine," Amino Acids: Biosynthesis and Genetic Regulation, 323-338, Hermann and Somerville, Eds., Addison-Wesley Publishing Co., Reading, MA.

Grossbard et al., "The Herbicide Glyphosate", Butterworths, London, 231-240 (1985).

Harring, et al., Accumulation of Shikimic Acid: A Technique for Screening Glyphosate Efficacy, J Agric. Food Chem., 46: 4406-4412 (1998).

Hasunuma, et al., "Replication of plasmid pSC101 in *Escherichia coli* K12: Requirement for dnaA function," Molec. Gen. Genet. 154: 225-230 (1977).

Henry, et al., "Shikimate accumulation in sunflower, wheat, and proso millet after glyphosate application," Weed Science, 55: 1-5 (2007).

Herrmann, K., "The Common Aromatic Biosynthetic Pathway," Amino Acids: Biosynthesis and Genetic Regulation, Hermann and Somerville, Eds., Addison-Wesley Publishing Co., Reading MA, 301-322 (1983).

Herrmann, K., "The Shikimate Pathway: Early Steps in the Biosynthesis of Aromatic Compounds," The Plant Cell, 7: 907-919 (1995).

Herrmann, K., "The shikimate pathway as an entry to aromatic secondary metabolism" Plant Physiol. 107: 7-12 (1995).

Herrmann, et al., "The Shikimate Pathway," Annual Review of Plant Physiology and Plant Molecular Biology, 50: 473-503 (1999).

Ikeda, M., "Amino Acid Production Process," Advances in Biochemical Engineering/Biotechnology, 79: 1-35 (2003).

Johansson, et al., "Transcriptome Analysis of a Shikimic Acid Producing Strain of *Escherichia coli* W3110 Grown Under Carbon- and Phosphate-Limited Conditions," J. Biotechnol, 126: 528-545 (2006).

Johansson, et al., "Shikimic Acid Production by a Modified Strain of *E. coli* (W3110.shik1) Under Phosphate-Limited and Carbon-Limited Conditions," Biotechnology and Bioengineering, 92: 541-552 (2005).

Kim, et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," Journal of American Chemical Society, 119: 681-690 (1997).

Kim, et al., "Structure-Activity Relationship Studies of Novel Carbocyclic Influenza Neuraminidase Inhibitors," Journal of Medicinal Chemistry, 41: 2451-2460 (1998).

Knop, et al., "Hydroaromatic Equilibration During Biosynthesis of Shikimic Acid," J. Am. Chem. Soc. 123: 10173-10182 (2001).

Kramer, et al., "Metabolic engineering for microbial production of shikimic acid," Metabolic Engineering, 5: 277-283 (2003).

McConkey, G.A., "Targeting the shikimate pathway in the malaria parasite *Plasmodium falciparum*," Antimicrob. Agents Chemother., 43(1): 175-177 (1999).

Mueller, et al., "Shikimate accumulates in both glyphosate-sensitive and glyphosate-resistant horseweed (*Conyza canadensis* L. Cronq.)," J. Agric. Food Chem., 51: 680-684 (2003).

Bresnahan, G.A., et al., "Glyphosate Applied Preharvest Induces Shikimic Acid Accumulation in Hard Red Spring Wheat (*Triticum aestivum*)," 2003, J Agric Food Chem, 51:4004-4007.

Kretzmer, K., et al., "Assay Comparison for Measuring Shikimate in Glyphosate-Treated Plant Species," 2007 North Central Weed Science Society Proceedings, 1 Pg.

Kruper, A., et al., "Facile and Economical Preparation of [14C]-Labelled Shikimic Acid," 1989, J Label Comp and Radiopharma, 28(6):714-718.

Stasiak, M.A., et al., "Alterations of Growth and Shikimic Acid Levels by Sublethal Glyphosate Applications on Pin Cherry and Trembling Aspen," 1991, Can J for Res, 21:1086-1090.

Tokhver, A.K., "Effect of Illumination Intensity and Light Quality on Accumulation of Shikimic Acid in Buckwheat Seedlings under the Influence of Glyphosate," 1990, Soy Plant Physiol, 37:542-546.

Velini, E.D., et al., "Glyphosate Applied at Low Doses Can Stimulate Plant Growth," 2008, Pest Manag Sci, 64:489-496.

International Search Report issued in PCT/US2008/080189, dated Apr. 3, 2009, 8 pages.

Written Opinion issued in PCT/US2008/080189, dated Apr. 3, 2009, 9 pages.

International Search Report issued in PCT/US2008/060079, dated Aug. 20, 2008, 7 pages.

Written Opinion issued in PCT/US2008/060079, dated Aug. 20, 2008, 7 pages.

FIG. 7

```
EcoRI
||||||
GAATTC-TTTTTGTTGACAGCGTGAAAACAGTACGGG pheL - phe leader peptide
                              MetLysHisIleProPhePhePheAlaPhe
 TAA
 |||
TACTGTACTAAAGTCACTTAAGGAAACAAACATGAAACACATACCGTTTTCTTCGCATTC PhePheThrPheProEnd
TTTTTTACCTTCCCCTGAATGGGAGGCGTTCGTCGTGTGAAACAGAATGCGAAGACGA RBS of the    start of
                                       pheA gene    pheA gene
                                       |||||||      Met
ACAATAAGGCCTCCCAAATCGGGGGCCTTTTTTATTGATAACAAAAGGCAACACTATG
```

PROCESSES FOR PRODUCING AND RECOVERING SHIKIMIC ACID

This application is a United States National Stage Application based on International Application No. PCT/US2008/080189, filed Oct. 16, 2008, and claims the benefit of U.S. Provisional Application Ser. No. 60/999,120, file Oct. 16, 2007, the entire contents of which are incorporated herein by reference.

FIELD OF THE INVENTION

The present invention generally relates to processes for producing and recovering cyclitolcarboxylic acids such as shikimic acid and quinic acid. In particular, the present invention is directed to processes for producing shikimic acid that comprise contacting glyphosate and an organism that has the common aromatic biosynthetic pathway. The present invention is also directed to recovery of the shikimic acid product from aqueous process streams utilizing membrane separation techniques.

BACKGROUND OF THE INVENTION

Shikimic acid (trihydroxy-1-cyclohexene-1-carboxylic acid; Chemical Abstracts Registry Number 138-59-0) is the key precursor compound for the synthetic manufacture of oseltamivir ((3R,4R,5S)-4-(acetyl-amino)-5-amino-3-(1-ethylpropoxy)-1-cyclohexene-1-carboxylic acid ethyl ester; Chemical Abstracts Registry Number 196618-13-0) (Rohloff et al., 1998; Federspiel et al., 1999). Oseltamivir, an orally active inhibitor of the essential neuraminidase of influenza virus, was discovered by scientists at Gilead Sciences Inc. of Foster City, Calif. (Kim et al., 1997; Kim et al., 1998; Abrecht et al., 2004; Bischofberger et al., U.S. Pat. No. 5,763,483; Lew et al., U.S. Pat. No. 5,866,601; Bischofberger et al., U.S. Pat. No. 5,952,375; Bischofberger et al., European Patent EP 0759917 B1; Bischofberger et al., European Patent EP 0976734 B1).

During influenza virus replication, new virus particles are bound to a sialic acid side-chain on the virus receptor protein. The mechanism of the viral neuraminidase is to cleave off this sialic acid and release the newly replicated virus particles. Oseltamivir is a sialic acid analog that inhibits this cleavage reaction by binding to the active site of the neuraminidase. These abortively infected cells are destroyed, stopping the spread of the virus within the host. Oseltamivir has potential use in influenza pandemics, including of "bird flu", in the form of the pharmaceutical TAMIFLU (De Clercq, 2002; Bradley, 2005; Farina and Brown, 2006). The pharmaceutical TAMIFLU is the phosphate salt of oseltamivir (Chemical Abstracts Registry Number 204255-11-8; also known as Roche compound Ro 64-0796/002 and Gilead Sciences compound GS-4104-02). TAMIFLU was first marketed by Roche in October 1999 (Farina and Brown, 2006). However, the large-scale production of the drug has been limited by the low availability of the shikimic acid precursor material.

Shikimic acid is a scarce and expensive chemical substance, being obtained principally from the seeds of woody shrubs, namely the Chinese star anise shrub (*Illicium verum*) native to China, and the shikimi-no-ki shrub (*Illicium anisatum*, formerly called *Illicium religiosum*) from whence shikimic acid got its name, native to Japan (Haslam, 1974; Sadaka and Garcia, 1999; Payne and Edmonds, 2005). About 30 kilograms of star anise or shikimi-no-ki seeds are required to produce one kilogram of shikimic acid (Farina and Brown, 2006). However, this natural source is limited, and insufficient to meet worldwide demand for TAMIFLU (Bradley, 2005).

1.3 grams of shikimic acid are required to manufacture the 10 doses of TAMIFLU needed to treat one person (Bradley, 2005). Production of a supply of TAMIFLU sufficient for treating 400 million people (a conservative estimate of the need in the event of an influenza pandemic) would require 520,000 kilograms of shikimic acid. Worldwide annual production of shikimic acid is currently only about 100,000 kilograms. Another estimate of the need for TAMIFLU in the event of a severe influenza pandemic is 30 billion doses, requiring 3.9 million kilograms of shikimic acid (Bradley, 2005).

Various approaches to resolving the problem of shikimic acid scarcity have been recently explored. One is the production of shikimic acid by microorganisms by a fermentation-based process (Farina and Brown, 2006). A fermentation-based process is described in Bogosian et al., International Patent Application No. PCT/US2008/060079, the entire contents of which are incorporated herein by reference for all relevant purposes and described below as the "fermentation method." Bogosian et al. includes a survey of fermentation-based processes, including citation of many related references, many of which are listed in the "REFERENCES" section elsewhere herein. Another method for production of shikimic acid is based on new chemical synthesis routes to oseltamivir phosphate that do not utilize scarce natural products as precursor compounds, but rather use inexpensive and widely available chemicals (Fukuta et al., 2006; Yeung et al., 2006). The chemical routes that have been developed to date are functional only as academic, bench-scale syntheses, and are not efficient industrial processes that could compete with the current shikimic acid-based manufacturing process for oseltamivir phosphate (Farina and Brown, 2006). Still other methods utilize plants for production of shikimic acid (as detailed below).

To understand the fermentation-based processes and other processes for production of shikimic acid, it would be useful to briefly review the biosynthetic pathway to shikimic acid. This pathway is known both as the common aromatic biosynthetic pathway (Herrmann, 1983; Pittard, 1987; Pittard, 1996) because it leads to (among other things) the aromatic amino acids, and also as the shikimate pathway (Haslam, 1974) after the metabolic intermediate in the pathway that was identified first. Several entire books and comprehensive review articles have been devoted to this important metabolic pathway (Haslam, 1974; Weiss and Edwards, 1980; Herrmann, 1983; Conn, 1986; Pittard, 1987; Haslam, 1993; Herrmann, 1995a; Herrmann, 1995b; Pittard, 1996; Herrmann and Weaver, 1999; Bongaerts et al., 2001; Kramer et al., 2003).

The common aromatic biosynthetic pathway is present in plants, bacteria, fungi, and other eukaryotic microorganisms. A search of on-line databases, specifically PubMed and the National Center for Biotechnology Information (NCBI), indicated that in addition to plants, bacteria, and fungi, the pathway is present in Stramenopiles such as brown algae and diatoms, Alveolata (within the Protista kingdom) such as ciliates, dinoflagellates and apicomplexa parasites, and various Euglenozoa. The common aromatic biosynthetic pathway in the bacterium *Escherichia coli* is shown in FIG. 1. The common aromatic biosynthetic pathway is not found in most higher animals, such as nematodes, insects and other arthropods, mollusks, and vertebrates and other chordates including fishes, amphibians, reptiles, birds and mammals. It has been established by others that the common aromatic biosynthetic pathway is present in the parasitic protozoan microorganisms known as apicomplexa (Roberts et al., 1998; McConkey, 1999; Roberts et al., 2002). It has also been suggested by others that the common aromatic biosynthetic pathway may be present in some higher animals, specifically in basal metazoans among the marine and freshwater invertebrates known as cnidarians (or coelenterates), including corals, sea anemones, jellyfishes, and hydroids (Starcevic et al., 2008). It is to be understood that statements that the common aromatic biosynthetic pathway is present in microorganisms mean that the pathway occurs in microscopic organisms and taxonomically related macroscopic organisms within the categories algae, Archaea, bacteria, fungi, and protozoa; this includes prokaryotes, including cyanobacteria, as well as unicellular eukaryotic organisms.

The fact that microorganisms possess the common aromatic biosynthetic pathway, and depend on it for the biosynthesis of many essential cellular components, and that mammals (including humans) lack the pathway, make the enzymes of the pathway attractive targets for new classes of antimicrobial therapeutic agents (Davies et al., 1994; Roberts et al., 1998). Any such therapeutic agents that are based on shikimic acid would increase the demand for shikimic acid. Indeed, 6-fluoroshikimic acid has been found to be an effective antibacterial compound (Davies et al., 1994; Bornemann et al., 1995) and anti-parasitical compound (McConkey, 1999; Roberts et al., 2002). Shikimic acid has also been converted into compounds that exhibited a significant inhibitory effect on cell proliferation, opening their possible use as anti-cancer chemotherapeutic agents (Tan et al., 1999). Thus, shikimic acid could serve as an important building block for a wide array of important classes of drugs, including anti-viral, anti-bacterial, anti-parasitical, and anti-cancer drugs.

As noted, other methods for production of shikimic acid utilize plants. In some plants and plant tissues, such as seeds, shikimic acid naturally accumulates to high levels. Chinese star anise and various species of evergreen trees are examples of these. Shikimic acid does not normally accumulate to detectable levels in, for example, vegetative tissues of important agronomic crops such as alfalfa, soybean, wheat, corn, sugar beet, etc.

Shikimic acid is a cyclitolcarboxylic acid, a class of compounds that also includes quinic acid. Quinic acid (1,3,4,5-tetrahydroxycyclohexane-1-carboxylic acid; Chemical Abstracts Registry Number 77-95-2) is also a starting material for the synthesis of various biologically important molecules, including oseltamivir. It is utilized in the synthesis of FK-506, an immune suppressive agent useful in preventing organ transplant rejection (Rao et al., 1991) and many natural products that are otherwise difficult to obtain, e.g., mycosporin (White et al., 1989) and D-myo-inositol-1,4,5-triphosphate (Falck et al., 1989). Quinic acid can be converted to shikimic acid (Dangschat et al., 1938 & 1950; and Adachi et al., 2006) and also to the methyl ester of shikimic acid (Cleophax et al., 1971 & 1973). Quinic acid is found in cinchona bark, coffee beans and the leaves of certain plants, and is made synthetically by hydrolysis of chlorogenic acid.

Glyphosate is well-known as a highly effective and commercially important herbicide useful for combating the presence of a wide variety of unwanted vegetation, including agricultural weeds (for example U.S. Pat. Nos. 3,799,758 and 4,405,531). Glyphosate and its various salts are essentially nonselective, meaning that when applied post-emergence they control a wide variety of annual and perennial weeds.

Glyphosate is a xylem and phloem mobile herbicide. Once absorbed by treated foliage, glyphosate is mobilized from treated leaves to other plant parts, such as roots or newly formed leaves. Mobilization from treated leaves will ultimately be limited by a direct herbicide effect on the treated leaves. When the herbicide effect is greater, the rate and extent of mobilization will be decreased. This effect on mobilization is greater with increased concentration of herbicide treatment, or when the environmental conditions at treatment are particularly stressful, such as under extreme dry, hot or cold conditions.

The mode of action of glyphosate is inhibition of the common aromatic biosynthetic pathway by inhibition of the chloroplast enzyme 5-enolpyruvylshikimate-3-phosphate synthase (EPSPS). Inhibition of EPSPS by glyphosate is non-reversible and treated plants are eventually "starved" of the essential end-products of the common aromatic biosynthetic pathway. Since this affects new growth to a greater extent than existing parts of the plant, the symptoms of glyphosate treatment appear to be slow to develop.

Shikimic acid is a natural product that does not normally accumulate to high levels in plants. However, when susceptible plants are treated with glyphosate, they accumulate shikimic acid (and also probably accumulate smaller amounts of the unstable metabolic intermediate 5-phosphoshikimic acid) to high levels. It is possible then, to use this system to produce large quantities of shikimic acid in any plant which is susceptible to glyphosate, both in plants which do not normally accumulate shikimic acid, and in plants which may naturally accumulate shikimic acid to some level. Further, if this method is applied to a normal agronomic crop system, including but not limited to soybean, alfalfa, corn, and wheat, it can be used to produce shikimic acid to industrial-scale levels and could potentially alleviate the limitation of shikimic acid in the production of products such as the neuraminidase inhibitor TAMIFLU.

Recently, with the bioengineering of glyphosate-resistant crops such as soybean, corn, cotton, canola, alfalfa, and sugar beet, glyphosate use has increased. When glyphosate is applied to glyphosate-resistant plants, no visual or biochemical injury symptoms are detected; however, any susceptible, undesirable plants (such as weeds) that may be present are controlled. The crops are still harvested in the conventional manner. For example in ROUNDUP READY Soybeans, the bean pods are harvested, and in ROUNDUP READY Cotton, the cotton bolls are collected. It is not typical to harvest the entire plant in such crops.

Previous research has identified shikimic acid accumulation in plants as a consequence of contacting a susceptible plant with glyphosate (see, for example, Amrhein et al., 1980; Harring et al., 1998; Pline et al., 2002; Mueller et al., 2003; Buehring et al., 2007; and Henry et al., 2007). Anderson et al. (2001) disclose a method for the determination of shikimic acid in plant tissue after exposure of the plant to glyphosate. Shikimic acid analysis of the plant tissue was performed using water extraction followed by high-performance liquid chromatography (HPLC) analysis. Anderson International Publication No. WO 2008/027570 A2 describes a method of isolating shikimic acid from a plant (wheat) that has been treated with glyphosate to increase the amount of shikimic acid in the plant.

Despite the knowledge of shikimic acid being present in plants treated with glyphosate, substantial efforts by others to develop new sources of shikimic acid have failed even though there has been a significant awareness and long-felt need for improved sources of shikimic acid, based on highly publicized concerns related to global pandemics of "bird flu" and other influenza-type viruses.

The research exemplified herein has shown that treatment of susceptible plants with glyphosate can also result in the accumulation of quinic acid. This accumulation of quinic acid provides a new source of quinic acid. It is possible then to treat susceptible plants with glyphosate to produce quinic acid on industrial-scale levels. The resulting quinic acid can be used in the production of bioactive chemical compounds such as FK-506 and TAMIFLU. Alternatively, the resulting quinic acid can be used to prepare shikimic acid which in turn may be used in the production of products such as TAMIFLU.

One object of the present invention is development of processes for production of shikimic acid and quinic acid utilizing plants. Another object of the present invention is development of processes for recovery of shikimic acid, regardless of the manner of its production (e.g., by the "plant method" or "fermentation method" as detailed elsewhere herein).

SUMMARY OF THE INVENTION

Briefly, therefore, the present invention is directed to processes for recovering shikimic acid.

In various embodiments, the present invention is directed to processes for recovery of shikimic acid from an aqueous process stream comprising shikimic acid and further comprising glyphosate. In one embodiment, the process comprises introducing the aqueous process stream into a membrane separation unit comprising at least one separation membrane; contacting the aqueous process stream and the at least one separation membrane to form a retentate and a permeate, wherein the retentate comprises shikimic acid and glyphosate; and separating shikimic acid from glyphosate in the retentate to form an aqueous product solution comprising shikimic acid and depleted in glyphosate relative to the retentate.

In another embodiment, the process comprises introducing the aqueous process stream into a membrane separation unit comprising at least one separation membrane; contacting the aqueous process stream and the at least one separation membrane to form a retentate and a permeate, wherein the permeate comprises shikimic acid and phenylalanine; and separating shikimic acid from phenylalanine in the permeate to form an aqueous product solution comprising shikimic acid and depleted in phenylalanine relative to the permeate.

In a further embodiment, the process comprises introducing the aqueous process stream into a membrane separation unit comprising at least one separation membrane; and contacting the aqueous process stream and the at least one separation membrane to form a retentate and a permeate.

In various other embodiments, the present invention is directed to processes for recovery of shikimic acid from a fermentation broth. In one embodiment, the process comprises introducing the fermentation broth into a membrane separation unit comprising at least one separation membrane; and contacting the fermentation broth and the at least one separation membrane to form a retentate and a permeate.

The present invention is further directed to methods for producing shikimic acid. In one embodiment, the method comprises (a) selecting a plurality of plant cells comprising the common aromatic biosynthetic pathway; (b) applying glyphosate to at least a portion of the plant cells; (c) harvesting the plant cells; and (d) extracting shikimic acid from the harvest.

In another embodiment, the method comprises (a) selecting a plurality of organisms comprising the common aromatic biosynthetic pathway; (b) harvesting the organisms; (c) applying glyphosate to at least a portion of the harvest; (d) performing an extraction process on the harvest; and (e) collecting shikimic acid produced by the extraction process.

In a further embodiment, the method comprises (a) applying glyphosate to at least a portion of a soybean plant; (b) harvesting at least a portion of the soybean plant; (c) extracting shikimic acid from the harvested portion of the soybean plant.

In a still further embodiment, the method comprises (a) harvesting at least a portion of a soybean plant; (b) applying glyphosate to at least a portion of the harvest; (c) performing an extraction process on at least a portion of the glyphosate treated harvest; (d) collecting shikimic acid produced by the extraction process.

The present invention is further directed to methods for producing quinic acid. In one embodiment, the method comprises (a) selecting a plurality of plant cells comprising the common aromatic biosynthetic pathway; (b) applying glyphosate to at least a portion of the plant cells; (c) harvesting the plant cells; and (d) extracting quinic acid from the harvest.

In another embodiment, the method comprises (a) applying glyphosate to at least a portion of a soybean plant; (b) harvesting at least a portion of the soybean plant; (c) extracting quinic acid from the harvested portion of the soybean plant.

The present invention is further directed to methods for producing a neuraminidase inhibitor. In one embodiment, the method comprises (a) selecting a plurality of organisms comprising the common aromatic biosynthetic pathway; (b) applying glyphosate to the organisms; (c) harvesting the organisms; (d) extracting shikimic acid from the harvest; (e) purifying the shikimic acid; and (f) converting the shikimic acid into a neuraminidase inhibitor.

In another embodiment, the method comprises (a) applying glyphosate to at least a portion of a soybean plant; (b) harvesting at least a portion of the soybean plant; (c) extracting shikimic acid from the harvested portion of the soybean plant; (d) purifying the shikimic acid; and (e) converting the shikimic acid into a neuraminidase inhibitor.

Other objects and features will be in part apparent and in part pointed out hereinafter.

BRIEF DESCRIPTION OF THE DRAWINGS

FIG. 7: As described in Example 5, alterations to the promoter region of the *E. coli* pheA gene carried on pXT1457 and pXT1483. Two regions were altered in the promoter region. A promoter-up mutation was introduced in the −10 region of the pheA promoter, changing it from TACTGTA to TATAATA. Also, a 146 by deletion was introduced between the pheA promoter and the ribosome binding site (RBS) of the pheA gene, removing the pheA attenuator region including the pheL leader peptide gene. Underlined nucleotides represent those nucleotides that were deleted. The EcoRI restriction site was placed where indicated, immediately before the promoter region of the pheA gene. SEQ ID NO: 4 is the nucleotide sequence listed in FIG. 7, while SEQ ID NO: 5 is the amino acid sequence listed in FIG. 7.

Corresponding reference characters indicate corresponding parts throughout the drawings.

DESCRIPTION OF THE SEQUENCE LISTING

Figure 1:
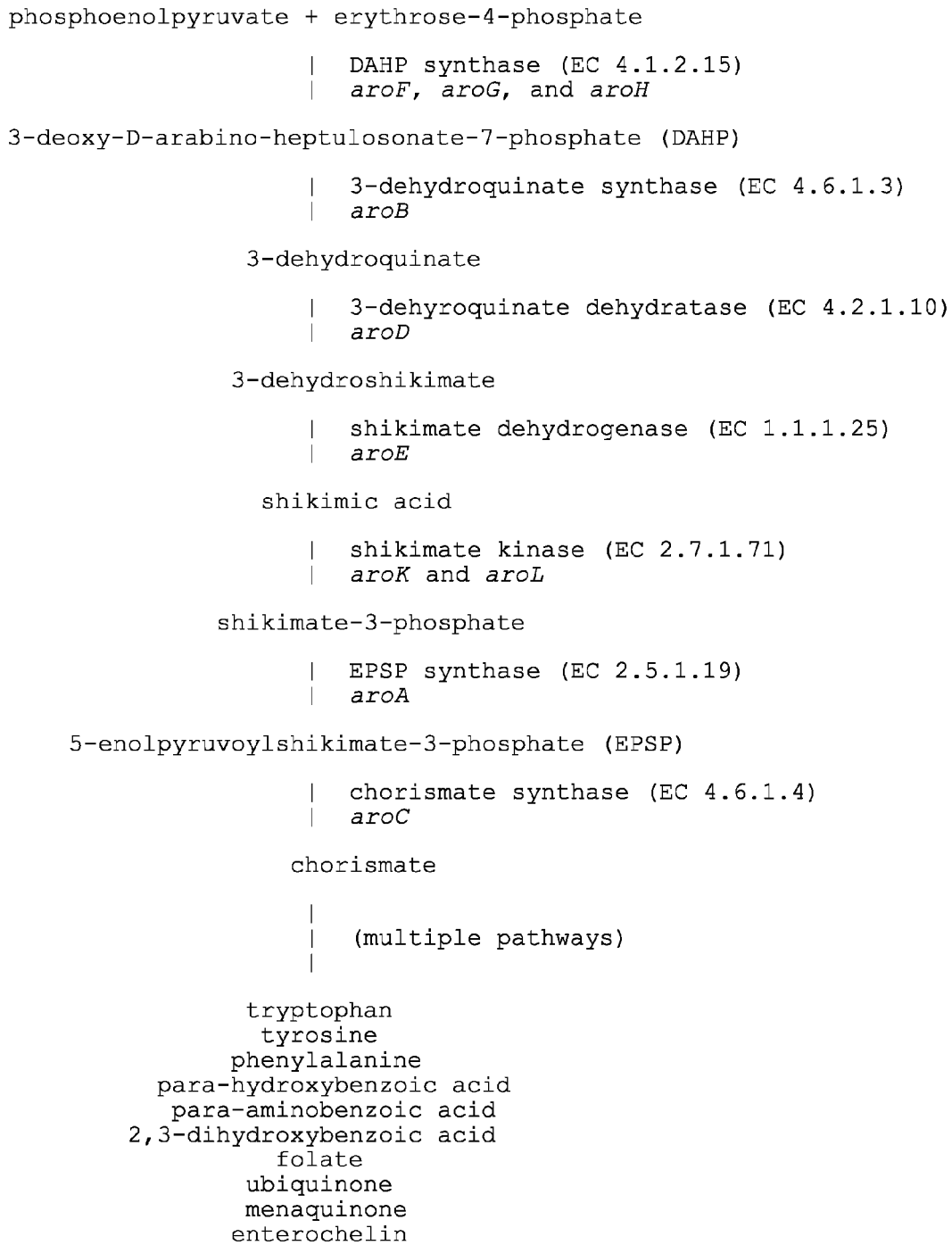
FIG. 1: The common aromatic biosynthetic pathway, also known as the shikimate pathway. The first step is the conversion of the central metabolites phosphoenolpyruvate and erythrose-4-phosphate into 3-deoxy-D-arabino-heptulosonate-7-phosphate (DAHP). Three more steps in the pathway yield shikimic acid, which in turn is converted in three additional steps to chorismic acid. Chorismic acid is a key intermediate in the biosynthesis of the aromatic amino acids tryptophan, phenylalanine, and tyrosine, as well as the other essential compounds para-hydroxybenzoic acid, para-aminobenzoic acid, 2,3-dihydroxybenzoic acid, and other compounds such as folate, ubiquinone, menaquinone, and enterochelin. In *Escherichia coli*, the first step in the common aromatic biosynthetic pathway is carried out by three isofunctional DAHP synthase enzymes; these three isofunctional enzymes are encoded by the aroF, aroG, and aroH genes. Similarly, there are two isofunctional enzymes of shikimate kinase, encoded by the aroK and aroL genes. The other enzymes of the pathway consist of single enzymes and are encoded by single genes: the aroB gene encodes 3-dehydroquinate synthase, the aroD gene encodes 3-dehydroquinate dehydratase, the aroE gene encodes shikimate dehydrogenase, the aroA gene encodes EPSP synthase, and the aroC gene encodes chorismate synthase.

SEQ ID NO: 1 Nucleotide sequence of the synthetic EcoRI-BamHI restriction fragment carried on the plasmids pXT1457 and pXT1483.

SEQ ID NO: 2 Amino acid sequence of the feedback-resistant *E. coli* chorismate mutase-prephenate dehydratase encoded on the plasmids pXT1457 and pXT1483.

SEQ ID NO: 3 Nucleotide sequence of the plasmid pXT1483.

SEQ ID NO: 4 Nucleotide sequence illustrating the alterations to the promoter region of the *E. coli* pheA gene carried on the pXT1457 and pXT1483 plasmids.

SEQ ID NO: 5 Amino acid sequence encoded by a portion of the deleted pheL leader peptide gene.

DEFINITIONS

The following definitions are provided to facilitate those skilled in the art to fully understand and appreciate the scope of the present invention. As suggested in the definitions provided below, the definitions provided are not intended to be exclusive, unless so indicated. Rather, they are preferred definitions, provided to focus the skilled artisan on various illustrative embodiments of the invention.

As used herein, the term "cyclitolcarboxylic acid" is limited to the group of carboxylic acids consisting of shikimic acid and quinic acid and refers not only to the free acid, but also to salts and esters thereof, unless the context dictates otherwise.

As used herein, the term "shikimic acid" refers not only to the free acid, but also to salts and esters thereof, unless the context dictates otherwise.

As used herein, the term "quinic acid" refers not only to the free acid, but also to salts and esters thereof, unless the context dictates otherwise.

As used herein, the term "derivative" when referring to shikimic acid or quinic acid means, without limitation, any chemical compound that is prepared from the free acid including salts and esters thereof and additionally for shikimic acid, the corresponding shikimate-3-phosphate. In particular, as used herein, the term "derivative of shikimic acid" refers, without limitation, to any chemical compound that is prepared using shikimic acid and/or shikimate-3-phosphate as starting reagents.

As used herein, the term "susceptible plant" refers to plants which contain the common aromatic biosynthetic pathway. In susceptible plants, treatment with glyphosate at levels at least of about 20 g a.e./ha will demonstrate substantial injury to the physiology of the plant. Susceptible plants may include annuals or perennials, grasses or broadleaves, seed bearing plants, grains, legumes, including both forage and grain legumes, woody plants, and trees.

As used herein, the term "resistant plant" refers to plants which tolerate glyphosate at levels less than about 3360 g a.e./ha. Examples of glyphosate resistant plants include transgenic soybeans and corn, such as for example ROUNDUP READY Soybean and ROUNDUP READY Corn available from Monsanto Company.

As used herein, the term "glyphosate" refers to N-(phosphonomethyl)glycine, a salt, ester or other derivative of N-(phosphonomethyl)glycine which is converted to glyphosate or which otherwise provides glyphosate anion. In this regard it is to be noted that the term "glyphosate" when used herein is understood to encompass N-(phosphonomethyl) glycine and such derivatives as well as mixtures thereof unless the context requires otherwise. Suitable salts of N-(phosphonomethyl)glycine include mono-, di- or tribasic forms and include organic ammonium, alkali metal, alkaline earth metal, ammonium (e.g., mono-, di- or triammonium) and sulfonium (e.g., mono-, di- or trimethylsulfonium) salts of N-(phosphonomethyl)glycine. The organic ammonium salts can comprise aliphatic or aromatic ammonium salts and can include primary, secondary, tertiary or quaternary ammonium salts. Specific representative examples of such organic ammonium salts include isopropylammonium, N-propylammonium, ethylammonium, dimethylammonium, 2-hydroxyethylammonium (also referred to as monoethanolammonium), ethylenediamine and hexamethylenediamine salts of N-(phosphonomethyl)glycine. Specific representative examples of alkali metal salts include potassium and sodium salts of N-(phosphonomethyl)glycine.

As used herein, the process of "harvesting" refers to collecting at least a portion of a plant for further use. Harvesting may include removing specific portions of a plant such as, for example, fruit, pods, kernels, seeds, leaves, stalks, needles, branches, twigs, or new growth. Harvesting may also include collecting whole plants or large portions of a plant containing a variety of plant tissues. In the case of plant cell cultures, harvesting may include further utilizing a portion of the cell culture or the entire cell culture. The plant material collected during the process of harvesting is referred to as "the harvest."

As used herein, the term "unicellular plant" refers to unicellular photosynthetic species and unicellular forms of cryptomonads, haptophytes, chrysophytes, euglenoids, dinoflagellates, diatoms, red algae, brown algae, and green algae.

As used herein, the term "multicellular plant" refers to multicellular photosynthetic species and multicellular forms (including colonies and filaments) of cryptomonads, haptophytes, chrysophytes, euglenoids, dinoflagellates, diatoms, red algae, brown algae, and green algae; bryophytes (including liverworts, hornworts, and mosses); seedless vascular plants (including psilotophytes, lycophytes, horsetails, and ferns); and seed plants (including cycads, ginkgo, conifers, gnetophytes, and angiosperms). Seed plants include, for example, coniferous vines, shrubs and trees, and annual, biennial, and perennial monocotyledonous and dicotyledonous angiosperm plants, including non-woody angiosperm plants, and woody angiosperm plants including deciduous and non-deciduous vines, shrubs, and trees.

As used herein, the term "microorganism" preferably refers to microscopic organisms and taxonomically related macroscopic organisms within the categories algae, Archaea, bacteria, fungi, Stramenopiles, Protista, and apicomplexa, that contain the common aromatic biosynthetic pathway, also known as the shikimate pathway. This definition includes all prokaryotes, including cyanobacteria and other bacteria, as well as all unicellular eukaryotic organisms, including Stramenopiles such as brown algae and diatoms, Alveolata (within the Protista kingdom) such as ciliates, dinoflagellates and apicomplexa parasites, and various Euglenozoa, that contain the common aromatic biosynthetic pathway.

As used herein, the term "minimal culture medium" preferably refers to a chemically defined culture medium. In such a culture medium, the chemical elements needed to support growth are provided by inorganic salts such as phosphates, sulfates, and the like. The carbon source is defined, and is usually a sugar such as glucose, lactose, galactose, and the like, or other compounds such as glycerol, lactate, acetate, and the like. While some such culture media also use phosphate salts as a buffer, other buffers may be employed such as citrate, triethanolamine, and the like.

As used herein, the terms "deregulate", "deregulation", "deregulated" and "deregulating" preferably refer to a deliberate increase of the flow of metabolites through a metabolic pathway, achieved by disabling one or more of the mechanisms that normally function to control such flow of metabolites. This deregulation may be achieved by disabling any of the mechanisms that repress the expression of any of the genes encoding any of the enzymes that carry out the steps of the metabolic pathway (referred to herein as "derepress" or "derepression" or "derepressed" or "derepressing"). This deregulation may also be achieved by rendering any of the enzymes, normally subject to feedback-inhibition by a metabolite in the pathway, resistant to such feedback-inhibition. Deregulation may also be achieved by any combination of derepression and feedback-inhibition mechanisms.

As used herein, the terms "optical density" and "OD" refer to an estimate of the concentration of cells of a microorganism suspended in a culture medium. Such optical density estimates are made spectrophotometrically and measure the decrease in transmitted light. Optical density is given by $\log_{10}(I_0/I)$, where $I_0$ is the intensity of the incident light, and I is the intensity of the transmitted light. For a given type of cell, the relationship between OD and cell concentration is linear over a wide range. As used herein, optical density measurements were made using light with a wavelength of 550 nanometers.

DETAILED DESCRIPTION OF THE PREFERRED EMBODIMENTS

Described herein are processes for producing and recovering cyclitolcarboxylic acids such as shikimic acid and quinic acid. Various embodiments of the present invention comprise producing shikimic acid by contacting an organism that undergoes the common aromatic biosynthetic pathway with glyphosate. For example, various embodiments of the present invention comprise contacting various legumes (e.g., soybeans) with glyphosate to enhance production of shikimic acid by inhibition of the common aromatic biosynthetic pathway. Various other embodiments of the present invention are directed to recovery of the shikimic acid product from aqueous process streams utilizing membrane separation techniques. The aqueous process streams comprise aqueous extracts of plant material contacted with glyphosate and aqueous fermentation broths produced by contacting a culture of a microorganism capable of producing shikimic acid (e.g., *Eschericia coli*) with glyphosate.

I. Cyclitolcarboxylic Acid Production from Plant Cells (The "Plant Method")

Generally, in certain embodiments, the present invention is directed to methods and processes for production of a cyclitolcarboxylic acid (e.g., shikimic acid and quinic acid) from plant material. Preparation of shikimic acid in this manner is generally referred to herein as the "plant method." Various embodiments of the plant method provide methods for producing the desired cyclitolcarboxylic acid wherein the method comprises: (a) cultivating a plurality of organisms such as, for example, plant material; (b) exposing at least a portion of the organisms to glyphosate; (c) extracting cyclitolcarboxylic acid from the treated organisms; (d) recovering and purifying the cyclitolcarboxylic acid; and (e) converting the cyclitolcarboxylic acid to a neuraminidase inhibitor such as for example, oseltamivir phosphate. Also, as detailed elsewhere herein, in accordance with the present invention, shikimic acid may be effectively recovered from aqueous process solutions comprising a cyclitolcarboxylic acid (e.g., shikimic acid) produced and extracted from plant material.

Alternative embodiments of the present invention provide methods for selecting a plurality of organisms comprising the common aromatic biosynthetic pathway, applying glyphosate to the organisms, harvesting material from the cultivated organisms, and extracting the desired cyclitolcarboxylic acid from the harvest.

Alternative embodiments of the present invention may include propagating a predetermined species, harvesting material from a cell culture, harvesting material from multicellular plants, or harvesting material from unicellular plants.

Alternative embodiments of the present invention may also include contacting or applying glyphosate to the organism such that the amount deposited on the organism is at least about 0.00001 grams per gram of organism. More preferably, the amount deposited is at least about 0.0001 grams or even at least about 0.001 grams glyphosate per gram of organism. Preferably, the amount of glyphosate deposited is less than about 0.1 grams per gram of organism.

In some embodiments of the present invention, the plurality of organisms (e.g., susceptible plants) is dispersed across at least one hectare to facilitate large scale production of shikimic acid. Alternative embodiments may include application of at least 10 grams of glyphosate per hectare (ha) of cultivated organism. More preferably, alternative embodiments may include at least about 100 grams of glyphosate per hectare of cultivated organism and less than about 10000 grams of glyphosate per hectare of cultivated organism. Embodiments of the invention comprising higher levels of glyphosate application will still be effective, but are not preferred due to excessive costs.

Harvesting of the glyphosate treated organisms may occur at any time after treatment of the susceptible organisms with glyphosate. Because the purpose of the claimed methods is to obtain shikimic or quinic acid from the treated organisms, if harvesting occurs after treatment of the susceptible organisms such harvesting occurs after a period of time sufficient to allow accumulation of either the shikimic or quinic, but prior to any possible decline in the amount of one or the other. Thus, the point at which the treated organisms are harvested may depend on a number of factors, including, for example, the type of organism, the concentration of glyphosate applied to the organism, the point of application of the glyphosate to the organism, and the environmental conditions surrounding the growth of the treated organism, both prior and subsequent to application of the glyphosate. Thus, in some embodiments of the present invention in which harvesting of the organism occurs after application of the glyphosate to the same, harvesting of the organisms occurs less than about 30 days after application of glyphosate. Preferably, harvesting occurs within about 21 days after application of glyphosate, more preferably within about 14 days after application of glyphosate, and still more preferably within about 7 days after application of glyphosate, (i.e. between about 0 and about 168 hours after the application of glyphosate). However, in some embodiments, harvesting the organism, such as, for example, plant material, may precede application of glyphosate. For example, glyphosate may be applied to plant material severed from the whole plant as long as the plant material maintains at least some metabolic processes. The period for which plant material maintains at least some metabolic processes may depend on a number of factors, including, for example, the species of plant material harvested, the part of the plant material harvested, the health of the plant material at the time of harvesting, and the conditions under which the harvested plant material is stored. Thus, once harvested, susceptible plant material may be contacted with glyphosate within minutes, to hours, to days after harvesting. In one embodiment, the harvested plant material may be contacted with glyphosate within about 60 minutes of harvesting. In another embodiment, the harvested plant material may be contacted with glyphosate within about 12 hours of harvesting. In another embodiment, the harvested plant material may be contacted with glyphosate within about 24 hours of harvesting. In another embodiment, the harvested plant material may be contacted with glyphosate within about 2 days of harvesting. In another embodiment, the harvested plant material may be contacted with glyphosate within about 5 days of harvesting. In another embodiment, the harvested plant material may be contacted with glyphosate within about 1 week of harvesting. Any method disclosed herein may utilize a step of harvesting the organism either before or subsequent to the application of glyphosate.

Alternative embodiments of the present invention include harvesting material from any plants containing the common aromatic biosynthetic pathway. Preferred embodiments of the present invention comprise plant species including photosynthetic protists (including cryptomonads, haptophytes, chrysophytes, euglenoids, dinoflagellates, diatoms, and unicellular species of algae), and multicellular plants including multicellular species of algae, bryophytes (including liverworts, hornworts, and mosses), seedless vascular plants (including psilotophytes, lycophytes, horsetails, and ferns), and seed plants (including cycads, ginkgo, conifers, gnetophytes, and angiosperms). Further preferred embodiments include coniferous vines, shrubs and trees, and annual, biennial, and perennial monocotyledonous and dicotyledonous angiosperm plants, including non-woody angiosperm plants, and woody angiosperm plants including deciduous and non-deciduous vines, shrubs, and trees. A preferred plant species is legumes, including both forage and grain legumes, including, for example, alfalfa, clover, peas, beans, lentils, lupins, mesquite, carob, and peanuts.

Specific non-limiting examples of alternative embodiments of the invention include alfalfa (*Medicago sativa*), soybeans (*Glycine max*), corn (*Zea mays*), canola (*Brassica napus*), cotton (species of the genus *Gossypium*), sugar beet (*Beta vulgarius*), wheat (*Triticum aestivum*), sunflower (*Helianthus annus*), velvetleaf (*Abutilon theophrasti*), barnyard grass (*Echinochloa crus-galli*), ryegrass (most species in the genus *Lolium*), switchgrass (*Panicum virgatum* and other species in the genus *Panicum*), sweetgum trees (*Liquidambar styraciflua* and other species in the genus *Liquidambar*), Chinese star anise shrubs (*Illicium verum*) and shikimi-no-ki shrubs (*Illicium anisatum*, formerly called *Illicium religiosum*, and other species in the genus *Illicium*). In various preferred embodiments, the plant material is harvested from a coniferous tree (e.g., pine, spruce, and fir trees). In various other preferred embodiments, the plant material is provided by soybeans.

Alternative embodiments of the present invention also include methods in which harvesting the organism does not kill the organism itself (i.e., harvesting only a portion of the organism, the remainder of the organism being capable of continued viability and/or possible production of additional portions which are harvested) or a majority of the organisms surrounding it. For example, when harvesting plants, such as, for example, perennial plants, it may be desirable for the plants to survive the current harvesting process for the purpose of enabling future harvesting from the same plant. In some alternative embodiments, survival of the plant may be enhanced by applying glyphosate to the harvested plant material (i.e., the harvested plant portion) only after the material has been removed from the remainder of the plant.

Alternative embodiments of the present invention include recovering and isolating the desired cyclitolcarboxylic acid produced by any of the methods described herein.

Alternative embodiments of the present invention may include embodiments wherein the harvest contains less than about 1000 μg quinic acid per gram fresh weight of harvest. Preferably, the harvest comprises a weight ratio of shikimic acid to quinic acid prior to extraction of at least about a 10:1. In some embodiments, the reduced level of quinic acid may allow for more efficient extraction and purification of the shikimic acid.

Alternative embodiments of the present invention include a method of producing the desired cyclitolcarboxylic acid comprising: (a) selecting a plurality of susceptible plants comprising the common aromatic biosynthetic pathway; (b) applying glyphosate to the plants; (c) harvesting the cultivated plants; and (d) extracting the cyclitolcarboxylic acid from the harvest.

Alternative embodiments of the present invention include a method of producing a neuraminidase inhibitor comprising: (a) selecting a plurality of organisms comprising the common aromatic biosynthetic pathway; (b) applying glyphosate to the organisms; (c) harvesting the organisms; (d) extracting shikimic acid from the harvest; (e) recovering the shikimic acid from the extract; and (f) converting the shikimic acid into a neuraminidase inhibitor.

Preferably, the embodiments of the present invention further comprise cultivating said organisms. More preferably, the method may comprise propagating a predetermined species.

In various aspects of embodiments of the invention, selecting a plurality of organisms may include identifying a particular species with beneficial characteristics, such as, for example, a rapid growth rate or beneficial processing characteristics, such as for example a particular species of plant. Furthermore, the process of selecting may include organisms which are already established, such as for example a pre-existing plant.

In various aspects of embodiments of the invention, selecting a plurality of organisms may include identifying a particular species of plant cells with beneficial processing characteristics for use in a cell culture.

In various aspects of embodiments of the invention, planting a field to be cultivated may include any techniques known in the art related to plant production, including the use of fertilizers, fungicides, insecticides, herbicides, and all other pesticides or products used in the production of agricultural crops.

Embodiments of the invention may include propagating any of a wide variety of susceptible plants comprising the common aromatic biosynthetic pathway, including but not limited to annual plants such as soybeans, corn, and cotton; perennial plants such as alfalfa; and woody plants such as shrubs and trees, including but not limited to conifers and deciduous species. In embodiments of the invention related to extraction of shikimic acid from trees, preferably the leaves or needles, fruits or nuts, and new growth are used. Alternatively, whole saplings may be used. In some embodiments, it may be preferable to apply the glyphosate early in the growing season when there is active elongation to maximize the effect of glyphosate and the resulting yield of shikimic acid. In some embodiments, portions of the plant may be treated with glyphosate and removed without killing the entire plant. In alternative embodiments, portions of the plant such as the leaves or needles may be removed from the plant prior to application of glyphosate.

In various aspects of embodiments of the invention, exposing plants or portions of plants may include typical means of herbicide application including but not limited to high pressure spraying from a vehicle, backpack or handheld spray equipment, and aerial application.

Other embodiments of the invention provide for methods of recovering and isolating the cyclitolcarboxylic acid after producing the cyclitolcarboxylic acid by any of the methods known in the art. Preferably, embodiments of the present invention are used to harvest and extract large volumes of material for the purposes of both efficiency and supplying the growing worldwide demand for shikimic acid. Preferably, embodiments of the present invention are used to extract at least about 1 kg of the cyclitolcarboxylic acid from plant material treated with glyphosate. More preferably, embodiments of the present invention are used to extract at least about 100 kg, still more preferably, at least about 1000 kg of the cyclitolcarboxylic acid from the plant material treated with glyphosate.

In various aspects of embodiments of the invention, the plants are treated with glyphosate by any means appropriate to mass production of cultivated plants, such as by spraying a dilute solution. Preferably, the solution comprises at least about 420 g a.e. glyphosate and is applied at a rate of at least about 95 L/ha. The glyphosate may be used at any effective concentration. In preferred embodiments of the invention plants are treated with glyphosate at a rate of 20-4200 g a.e./ha. In more preferred embodiments the plants are treated with glyphosate at a rate of 210-3360 g a.e./ha. In an even more preferred embodiment of the invention glyphosate is applied at a rate of 420-1680 g a.e./ha. In the most preferred embodiment of this invention glyphosate is applied at a rate of 840 g a.e./ha.

Preferably, the formulation of glyphosate comprises additional components intended to improve the efficiency and efficacy of application. Preferable formulations of glyphosate include the addition of a sufficient amount of water to form a dilute solution of about 0.5 g a.e./L-5.0 g a.e./L concentration. Preferably formulations of glyphosate may also include a variety of surfactants, including alcohol alkoxylates, alkylphenol alkoxylates, fatty amine alkoxylates, triglyceride ethoxylates, sulfates, sulfonates, phosphate esters, quaternary amine ethoxylates, amine oxides, alkyl polyglycosides, and etheramine ethoxylates. Additional components which may also be incorporated into the glyphosate formulation include dyes, antifoams, solvents, densifiers, and chelators. In the case of plants with higher levels of epicuticular wax and/or a reduced planar surface, such as, for example, pine needles, an aggressive surfactant or a higher concentration of surfactant may be preferred. Alternatively, for large woody plants glyphosate can be applied to a hole created in a woody stalk such as a tree trunk.

In preferred embodiments of the invention, the cyclitolcarboxylic acid is extracted from the treated plant material using any of several methods known in the art including, but not limited to, freeze thaw extraction using HCl, solvent extraction using tridodecylamine, or lipid extraction using liquefied petroleum gas and ethanol. Extraction may be accomplished by any means known in the art including techniques such as are described in Chinese patent application 1830939A, International Patent Application Publication Nos. WO 01/68891, WO 07/077,570, and WO 02/06203, and U.S. Patent Application Publication Nos. 2007/0149805, 2004/0009242, 2002/0155177, 2002/0114853, 2007/0087424 and 2007/0161818.

One example of a preferred method for extracting shikimic acid from plant material treated in accordance with the present invention includes freezing the harvested stems and leaves of the plants (e.g., at temperatures of approximately −80° C.). The frozen stems and leaves are typically ground and the plant extract mixture prepared by extraction of the ground plant material using an aqueous HCl solution (e.g., 0.25 N) in a weight:weight (solution:plant material) of about 100:1. The solution containing the plant material can be agitated (e.g., in a blender) to assist in the release of soluble content from the plant cells. Plant material is separated from the resulting mixture using suitable apparatus (e.g., a centrifuge such as a Beckman Coulter Avanti J—20I model centrifuge operated at 12,000×g for 30 min at 4° C.) to remove cellular debris. The resulting supernatant or centrate can be optionally filtered (e.g., using a MAXICULTURE Capsule 0.2 μm or 0.45 μm filter).

In preferred embodiments of the invention, at least about 1 kg of the cyclitolcarboxylic acid is extracted from the treated plant material. Once extracted, the shikimic acid may be incorporated into an aqueous process stream for recovery of shikimic acid as detailed elsewhere herein.

II. Shikimic Acid Production from Microorganism Cultures (The "Fermentation Method")

As detailed elsewhere herein, in accordance with the present invention, shikimic acid may be recovered from process solutions comprising shikimic acid produced from microorganism cultures. Preparation of shikimic acid in this manner is generally referred to herein as the "fermentation method." Suitable fermentation methods are described in Bogosian et al., International Application No. PCT/US2008/060079, the entire contents of which have been incorporated herein by reference.

Various embodiments of the fermentation method provide methods for producing shikimic acid comprising: a) providing a microorganism culture; wherein the microorganism is capable of converting shikimate-3-phosphate to shikimic acid; b) contacting the microorganism with glyphosate; and c) converting shikimate-3-phosphate to shikimic acid. In preferred aspects of these embodiments the microorganism is *Escherichia coli* (*E. coli*). In more preferred aspects of these embodiments of the invention the microorganism is *E. coli* strain LBB427. In ever more preferred aspects of these embodiments of the invention the microorganism is *E. coli* strain LBB427 transformed with the plasmid pXT1457 or with the plasmid pXT1483.

In various aspects of these embodiments of the invention, the conversion of shikimate-3-phosphate to shikimic acid may be accomplished by any suitable mechanism including, but not limited to, enzymatic methods, chemical methods, and/or physical methods (examples include, but are not limited to enzymatic conversion and heating in a low pH environment). In preferred aspects of this embodiment of the invention, the conversion is through an enzymatic catalysis. In especially preferred aspects of this embodiment the enzymatic conversion is accomplished by a phosphatase (e.g. an alkaline phosphatase). In all embodiments of the invention the conversion of shikimate-3-phosphate may take place either intra-cellularly or extra-cellularly. Moreover, the instant invention envisions the conversion step occurring either with or without the isolation of shikimate-3-phosphate. That is, various embodiments of the invention provide for the production of shikimate-3-phosphate by any of the methods described herein, purification of shikimate-3-phosphate and subsequent hydrolysis of shikimate-3-phosphate to shikimic acid by any suitable method known to those skilled in the art.

In another aspect of these embodiments of the invention, conversion of shikimate-3-phosphate to shikimic acid may be accomplished by physical means. It has been reported that shikimate-3-phosphate can be converted to shikimic acid by lowering the pH and/or raising the temperature of culture samples in which the microorganisms are grown. (Davis and Mingioli, 1953) Thus, in certain embodiments conversion of shikimate-3-phosphate to shikimic acid is accomplished by lowering the pH of the culture medium and/or increasing the temperature of the culture medium. These adjustments to the pH and/or temperature of the culture medium are made subsequent to the contact of the microorganism in the medium with glyphosate, and before recovery of the shikimic acid from the microorganism or medium. Generally, the pH of the medium may be lowered to below the typical cell culture growth pH of about 7, and preferably lowered to a pH of about 1. Generally, the temperature of the medium may be raised to a temperature greater than the typical cell culture growth temperature of about 37° C., and preferably to a temperature of at least about 60° C.

Other embodiments of the fermentation method include recovering and/or purifying shikimic acid after producing it by any of the fermentation methods described herein.

Other embodiments of the instant invention provide fermentation methods for producing shikimic acid from microorganisms where the method comprises: a) deregulating a microorganism's common aromatic biosynthetic pathway; b) contacting the microorganism with glyphosate; and c) converting shikimate-3-phosphate to shikimic acid. In preferred aspects of this embodiment of the invention the microorganism is *Escherichia coli* (*E. coli*). In more preferred aspects of these embodiments of the invention the microorganism is *E. coli* strain LBB427. In even more preferred aspects, the microorganism is *E. coli* strain LBB427 transformed with the plasmid pXT1457 or with the plasmid pXT1483. In any of the aspects of these embodiments of the invention the shikimate-3-phosphate may be converted to shikimic acid by any suitable method. Preferably, the conversion of shikimate-3-phosphate to shikimic acid is by a chemical, physical and/or enzymatic method. Preferably, the shikimate-3-phosphate is converted to shikimic acid by a phosphatase enzyme; more preferably by an alkaline phosphatase enzyme.

Some aspects of the fermentation method comprise deregulating the biosynthesis of one or more compound selected from the group consisting of tryptophan, phenylalanine, tyrosine, shikimic acid, shikimate-3-phosphate, 5-enolpyruvoylshikimate-3-phosphate, chorismic acid, para-hydroxybenzoic acid, para-aminobenzoic acid, 2,3-dihydroxybenzoic acid, folate, ubiquinone, menaquinone, and enterochelin. In preferred aspects of this embodiment of the invention the deregulation is carried out in a bacterium, preferably in *E. coli*.

In various embodiments of the fermentation method, the biosynthesis of phenylalanine is deregulated in a microorganism. In preferred aspects of this embodiment the microorganism is *Escherichia coli* (*E. coli*). In more preferred aspects of this embodiment of the invention the microorganism is *E. coli* strain LBB427. In even more preferred aspects of this embodiment of the invention the microorganism is *E. coli* strain LBB427 transformed with the plasmid pXT1457 or with the plasmid pXT1483.

In various aspects of the fermentation method, the microorganism is contacted with glyphosate by adding it to the culture medium. The glyphosate may be used at any effective concentration. In preferred embodiments of the invention the glyphosate is added at a concentration of 1 millimolar or greater. In more preferred embodiments the glyphosate is added at a concentration of 10 millimolar or greater. In other preferred embodiments of the invention the glyphosate is added at a concentration of from about 10 millimolar to about 50 millimolar; more preferably, the glyphosate is added at a concentration of from about 20 millimolar to about 50 millimolar. In an especially preferred embodiment of the invention the glyphosate is added at a concentration of about 20 millimolar.

Shikimic acid and/or shikimate-3-phosphate is typically recovered from the culture medium or culture supernatant about 5 hours subsequent to the exposure of the medium or the microorganisms therein to glyphosate. Yield of shikimic acid and/or shikimic-3-phosphate may be optimized relative to the particular microorganism utilized by shortening or lengthening the period of time between glyphosate exposure and shikimic acid and/or shikimic-3-phosphate recovery. Shikimic acid and/or shikimate-3-phosphate concentration in the culture medium tends to increase for a period of time following glyphosate exposure and then plateaus. Adjustments to the time period based on the particular microorganism utilized to optimize recovery can be readily determined by one skilled in the art.

In preferred aspects of these embodiments of the invention the microorganism is grown in a minimal culture medium. The microorganism may be grown using any suitable method known to those of skill in the art. In preferred embodiments of the invention the microorganisms are produced using either a shaker flask or a fermentation based process (i.e. in a controlled bioreactor) wherein the microorganism is grown to an optical density (O.D.) of greater than two (2); preferably an O.D. of greater than 10, greater than 20, greater than 50, or greater than 100.

In any aspect of the instant invention the fermentation-based culture may be used to produce shikimic acid at a rate of greater than 1 gram/liter, preferably greater than about 20 grams/liter; more preferably, greater than about 40 grams/liter; greater than 90 grams/liter; or greater than 100 grams/liter.

In various aspects of the invention the microorganism may be algae, Archaea, bacteria, fungi, or protozoa; including prokaryotes, cyanobacteria, and unicellular eukaryotic organism.

III. Recovery of Cyclitolcarboxylic Acid

Processes of the present invention for recovering a cyclitolcarboxylic acid such as shikimic acid generally comprise contacting an aqueous process stream comprising shikimic acid and a separation membrane to form a retentate and a permeate. The aqueous process stream comprises water and the extract of plant material produced in accordance with the plant method and/or culture medium or culture supernatant produced in accordance with the fermentation method. The retentate and permeate compositions depend on a variety of factors, including the origin and composition of the process stream initially contacted with the membrane. In various embodiments, the shikimic acid recovered as the product is present in the retentate, whereas in various other embodiments the recovered shikimic acid is present in the permeate. The retentate or permeate comprising the shikimic acid may be further treated by a variety of methods including, for example, concentration and ion exchange methods (as detailed elsewhere herein) to recover a shikimic acid product of the desired purity. It is to be understood that reference to the presence of a particular cyclitolcarboxylic acid such as shikimic acid within a particular stream (e.g., retentate or permeate) does not indicate the absence of shikimic acid in other process streams. However, as detailed elsewhere herein, the stream from which the product shikimic acid is recovered is often selected in view of other features besides the concentration or proportion of shikimic acid including, for example, the presence of other components, the relative proportions of these components and shikimic acid, and the ease with which the shikimic acid may be separated from these other components.

Various conventional methods for recovery of shikimic acid utilize organic solvents. Generally in accordance with the present invention and as described above, the aqueous process stream comprises an aqueous plant extract or cell culture medium or supernatant prepared in the absence of organic solvents. Thus, the present invention provides a water-based separation and recovery process for shikimic acid that avoids the cost, disposal, and separation issues associated with organic solvents. Furthermore, in this manner, the process of the present invention may be readily utilized in connection with any aqueous stream containing shikimic acid. More particularly, much of the discussion herein focuses on aqueous process streams containing shikimic acid produced in accordance with the plant method and fermentation methods detailed herein, but is likewise to be understood that the processes and methods of the present invention are suitable for treatment of any aqueous process stream containing shikimic acid, regardless of the source.

Generally, in accordance with the present invention, any of a variety of membrane separation techniques well-known in the art may be utilized including, for example, ultrafiltration, microfiltration, nanofiltration, and reverse osmosis. However, in various preferred embodiments, the process of the present invention utilizes nanofiltration. Suitable nanofiltration separation membranes are typically constructed of organic polymers such as crosslinked aromatic polyamides in the form of one or more thin film composites. Generally, suitable nanofiltration membranes exhibit a Molecular Weight Cut Off (MWCO) of from about 150 daltons to about 1000 daltons and, typically, of about 250 daltons. In addition to the size of process stream components or constituents, separation by suitable nanofiltration membranes also typically includes a component based on the charge of the membrane, which depends, at least in part, on the pH of the process stream contacted with the membrane. The pH of the process stream also typically impacts the extent of dissociation of acidic components of the process stream. Thus, as detailed elsewhere herein, the pH of the process stream impacts separation of process stream components. Adjustment of process stream pH may be suitably conducted in accordance with methods known to one skilled in the art by an addition of an appropriate acidic or basic reagent prior to contacting the separation membrane.

Examples of suitable nanofiltration membranes include, for example and without limitation, the D H and K series membranes manufactured by GE Water & Process Technologies, Inc., a subsidiary of GE Infrastructure (Minnetonka, Minn.), SelRO membranes available from Koch Membrane Systems (Wilmington, Mass.), and the NF membranes available from Filmtec Corporation, a subsidiary of the Dow Chemical Company (Midland, Mich.). Specific examples of suitable nanofiltration membranes include, for example and without limitation, the DK, DL, HK, HL and KH membranes manufactured by GE Water & Process Technologies, Inc., the NF membranes (e.g., NF 40, NF 40HF, NF 50, NF 70, and NF 270) available from FilmTec Corporation, MPS-34 membrane available from Koch Membrane Systems (Wilmington, Mass.), the SU 600 membrane available from Toray (Japan), and the NTR membranes (e.g. NTR 7450 and NTR 7250) available from Nitto Electric (Japan).

In addition to shikimic acid and glyphosate, the process stream to be treated may comprise one or more inorganic salts. These salts may be present as a result of utilizing a glyphosate salt in the method for producing shikimic acid (i.e., by the plant method or fermentation method) and may also be native to plants used to produce shikimic acid. These salts generally comprise potassium chloride, ammonium chloride, ammonium hydroxide, sodium sulfate, potassium sulfate, and combinations thereof. It has been observed that the relative proportions of shikimic acid and salts in the process stream impact whether the product shikimic acid tends to accumulate in the retentate or permeate produced upon contact with the separation (e.g., nanofiltration) membrane. For example, in various embodiments, it has generally been observed that as the relative proportion of shikimic acid to inorganic salts decreases, the proportion of shikimic acid in the retentate increases. Conversely, it has likewise generally been observed that as the relative proportion of shikimic acid to inorganic salts increases, the proportion of shikimic acid in the permeate increases.

Regardless of how the shikimic acid in the aqueous process stream is produced (i.e., by the plant method or fermentation method), the process stream to be treated further comprises glyphosate. As with inorganic salts, the proportion of glyphosate in the process stream and, more particularly, the relative proportion of shikimic acid and glyphosate in the process stream impacts whether the desired product shikimic acid tends to accumulate in the retentate or permeate. For example, in various embodiments, it has generally been observed that as the relative proportion of shikimic acid to glyphosate increases, the proportion of shikimic acid in the retentate increases. Conversely, it has likewise generally been observed that as the relative proportion of shikimic acid to glyphosate decreases (e.g., to near equivalent shikimic acid and glyphosate contents, by weight), the proportion of shikimic acid in the permeate increases.

Suitable nanofiltration membranes typically exhibit the following rejection characteristics with respect to shikimic acid, inorganic salts, and glyphosate, as determined from compositional data for the initial process stream and resulting retentate and permeate. These compositional data may be determined by methods known in the art including, for example, high performance liquid chromatography (HPLC) and mass spectrometry analysis. A rejection characteristic may be defined as the difference between one and the ratio of permeate concentration (Cp) of a component to the average of the process stream concentration (Cs) and retentate concentration (Cr) of the component: 1−Cp/((Cs+Cr)/2). Suitable nanofiltration membranes generally exhibit a rejection characteristic with respect to shikimic acid of from about 40% to about 100%, typically from about 60% to about 80% and, more typically, of about 70%. With respect to inorganic salts, suitable nanofiltration membranes generally exhibit a rejection characteristic of from about 20% to about 80%, typically from about 40% to about 60% and, more typically, of about 50%. The glyphosate rejection characteristic of suitable nanofiltration membranes is generally from about 75% to about 100%, typically from about 90% to about 98% and, more typically, about 95%.

In addition to the components of the process stream from which the shikimic acid is recovered (and their relative proportions), the pH of the process stream contacted with the separation membrane also impacts whether the desired product shikimic acid is present or accumulates in the retentate or permeate. For example, it has been observed that contacting a process stream having a pH of about 4 and a nanofiltration separation membrane as described herein, generally provides a permeate containing product shikimic acid. Conversely, more acidic and more basic process streams having a pH of less than about 4 (e.g., from about 1 to about 3.5) or greater than about 4 (e.g., from about 4.5 to about 7) have been observed to provide a retentate containing product shikimic acid. Without being bound to a particular theory, this effect of pH on the retention of shikimic acid is currently believed to be due, at least in part, to the effect of the pH of the process stream on the surface charge of the membrane and the degree of dissociation of components of the process stream, including dissociation of shikimic acid.

In various embodiments in which shikimic acid is recovered from an aqueous process stream comprising culture medium or culture supernatant produced by the fermentation method, the process stream typically includes one or more other impurities in addition to glyphosate and inorganic salts. For example, the aqueous process stream typically contains phenylalanine produced during fermentation. As detailed elsewhere herein, in those embodiments in which the shikimic acid is provided by the fermentation method, the desired product shikimic acid is typically present in the permeate. The rejection characteristic of the separation membrane with respect to phenylalanine is typically higher than the rejection characteristic for shikimic acid. For example, the phenylalanine rejection characteristic of suitable nanofiltration membranes is generally from about 70% to about 100%, typically from about 85% to about 95% and, more typically, about 90%. However, along with shikimic acid, the permeate will typically likewise comprise some phenylalanine. In accordance with the present invention it has been discovered that controlling the pH of the aqueous process stream contacted with the separation membrane provides advantageous selective retention by the membrane of phenylalanine over desired product shikimic acid. For example, it has been observed that an aqueous process stream having a pH of about 4 and comprising phenylalanine provides advantageous relative transmission of shikimic acid over phenylalanine. More particularly, it has been observed that contacting an aqueous process stream at such pH levels and a separation membrane minimizes the ratio of the shikimic acid rejection characteristic to the phenylalanine rejection characteristic. More particularly, in accordance with various preferred embodiments, this ratio is preferably less than about 0.90, more preferably less than about 0.80 and, still more preferably, about 0.70.

Plant Method

In various embodiments in which shikimic acid is recovered from an aqueous process stream comprising the extract of plant material produced by the plant method, a retentate comprising desired product shikimic acid is provided by a process stream exhibiting one or more of the following characteristics. In various such embodiments, the process stream has a pH of from about 2 to about 7, from about 3.5 to about 5.5, or about 5. Generally in accordance with these embodiments the process stream contains shikimic acid at a concentration of from about 0.05 to about 1.2 wt. %, and typically from about 0.05 to about 1 wt. %. Further in accordance with these embodiments, the process stream contains glyphosate at a concentration of from about 0.02 to about 1 wt. %, from about 0.02 to about 0.5 wt. %, or from about 0.03 to about 0.25 wt. %. Further in accordance with such embodiments, the concentration of inorganic salts is typically from about 0.1 to about 1.5 wt. %, and more typically from about 0.5 to about 1 wt %.

Further in accordance with these embodiments, the weight ratio of shikimic acid to inorganic salts is typically less than about 1, more typically less than about 0.5 and, still more typically, less than about 0.25. The weight ratio of shikimic acid to glyphosate is typically at least about 5, more typically at least about 10 and, still more typically, at least about 20 (e.g., from about 20 to about 30).

Further in accordance with such embodiments, the ratio of the membrane's shikimic acid rejection characteristic to its glyphosate rejection characteristic is generally from about 0.60 to about 0.90, and typically from about 0.70 to about 0.80. Further in accordance with these embodiments, the ratio of the membrane's shikimic acid rejection characteristic to its inorganic salts rejection characteristic is generally from about 1.0 to about 2.5, and typically from about 1.6 to about 2.0.

In view of the typically relatively low concentration of shikimic acid in the aqueous process stream and the rejection characteristics of the membrane with respect to shikimic acid, a substantial portion of the initial shikimic acid is present in the retentate while the permeate includes a relatively low proportion of shikimic acid. The rejection characteristics of the membrane for glyphosate provide a retentate that likewise includes a substantial fraction of the initial glyphosate content. However, as detailed elsewhere herein, product shikimic acid may be recovered from the retentate by separating the glyphosate and shikimic acid by methods known in the art including, for example, ion exchange.

Further in accordance with these plant method embodiments, the concentration of shikimic acid in the retentate is generally from about 0.05 to about 1.5 wt. %, and typically from about 0.25 to about 1 wt. %. The concentration of glyphosate in the retentate is generally from about 0.002 to about 0.025 wt. %, and typically from about 0.01 to about 0.025 wt. %. Further in accordance with these embodiments, the concentration of inorganic salts in the retentate is generally from about 0.6 to about 1.2 wt. %, and typically from about 0.8 to about 1 wt. %. The pH of the retentate is generally from about 2 to about 7, and typically from about 3.5 to about 5.5.

Additionally or alternatively, further in accordance with these embodiments, the concentration of shikimic acid in the permeate is generally from about 0.025 to about 1 wt. %, and typically from about 0.25 to about 0.75 wt. %. The concentration of glyphosate in the permeate in these embodiments is generally from about 0.002 to about 0.025 wt. %, and typically from about 0.01 to about 0.025 wt. %. Further in accordance with these embodiments, the concentration of inorganic salts in the permeate is generally from about 0.1 to about 0.3 wt. %.

Fermentation Method

In various embodiments in which shikimic acid is recovered from an aqueous process stream comprising the culture medium or culture medium supernatant produced by the fermentation method, a permeate comprising desired product shikimic acid is provided by a process stream exhibiting one or more of the following characteristics. In various such embodiments, the process stream has a pH of from about 2 to about 7, from about 3.5 to about 4.5, or about 4. Generally in accordance with these embodiments, the process stream contains shikimic acid at a concentration of about 0.4 to about 5 wt. %, and typically from about 0.5 to about 2.5 wt. %. Further in accordance with these embodiments, the process stream typically contains glyphosate at a concentration of from about 0.2 to about 0.5 wt. %, and more typically from about 0.3 to about 0.4 wt. % (e.g., about 0.35 wt. %). The concentration of inorganic salts in the process stream in these embodiments is typically from about 0.1 to about 1 wt. %, and more typically from about 0.4 to about 0.8 wt. % (e.g., about 0.6 wt. %). Also in accordance with these embodiments, the process streams typically contains phenylalanine at a concentration of from about 0.5 to about 4 wt. %, and more typically from about 1 to about 3 wt. %.

Further in accordance with these embodiments, the weight ratio of shikimic acid to inorganic salts is typically at least about 0.5, more typically at least about 1 and, still more typically, at least about 1.5. The weight ratio of shikimic acid to glyphosate is typically from about 1 to about 5, more typically from about 2 to about 4 and, still more typically, about 3. Further in accordance with these embodiments, the weight ratio of shikimic acid to phenylalanine is generally from about 0.1 to about 10, or from about 1 to about 5. In various other embodiments, the weight ratio of shikimic acid to phenylalanine is from about 0.5 to about 1.5, or from about 0.8 to about 1.2. As noted above in accordance with embodiments in which the aqueous process stream is provided by the fermentation method, advantageous selective retention of phenylalanine by the membrane over passage of shikimic acid has been observed at pH levels of about 4.

Further in accordance with such embodiments, the ratio of the membrane's shikimic acid rejection characteristic to its glyphosate rejection characteristic is generally from about 0.6 to about 0.9, and typically from about 0.6 to about 0.8 or from about 0.6 to about 0.7. The ratio of the membrane's shikimic acid rejection characteristic to its inorganic salt rejection characteristic is generally from about 1.25 to about 2, and typically from about 1.4 to about 1.8. Further in accordance with such embodiments, the ratio of the membrane's shikimic acid rejection characteristic to its phenylalanine rejection characteristic is generally from about 0.1 to about 1, and typically from about 0.7 to about 0.9 or from about 0.7 to about 0.8.

The typically higher concentration of shikimic acid in the aqueous process stream as compared to process streams comprising the extract of plant material produced by the plant method generally provides a permeate containing a greater proportion (mass basis) of shikimic acid. Accordingly, the permeate comprises a suitable proportion of shikimic acid to provide the desired product shikimic acid. In view of the rejection characteristics of the membrane for glyphosate (e.g., about 95%), the retentate includes a substantial fraction of the initial glyphosate content. Thus, in accordance with these embodiments, contacting an aqueous process stream having the noted characteristics generally provides substantial separation of desired product shikimic acid and glyphosate in the permeate. As detailed elsewhere herein, product shikimic acid present in the permeate may be recovered by separating phenylalanine and shikimic acid by methods known in the art including, for example, ion exchange.

Further in accordance with these fermentation method embodiments, the concentration of shikimic acid in the retentate is generally from about 0.4 to about 6 wt. %, and typically from about 2 to about 4 wt. %. The concentration of glyphosate in the retentate is generally from about 0.3 to about 0.5 wt. %. Further in accordance with these embodiments, the concentration of phenylalanine in the retentate is generally from about 0.5 to about 5 wt. %, and typically from about 1.5 to about 3 wt. %. The concentration of inorganic salts in the retentate is generally from about 0.5 to about 1 wt. %.

Additionally or alternatively, the concentration of shikimic acid in the permeate is generally from about 0.25 to about 3.5 wt. %, and typically from about 1 to about 2.5 wt. %. Further in accordance with these embodiments, the concentration of glyphosate in the permeate is generally from about 0.25 to about 0.4 wt. %. The concentration of phenylalanine in the permeate is generally from about 0.4 to about 3.6 wt. %, and typically from about 1 to about 2.5 wt. %. The concentration of inorganic salts in the permeate is generally from about 0.2 to about 0.5 wt. %. The pH of the permeate is generally from about 2 to about 7, and typically from about 3.5 to about 4.5, or about 4.

In accordance with these and various other embodiments detailed elsewhere herein, contacting the process stream and selective membrane generally provides a permeate depleted in shikimic acid relative to the aqueous process stream. In this regard it is to be understood that reference to a permeate "depleted" in shikimic acid as compared to the process stream does not necessarily indicate that the permeate includes shikimic acid at a reduced concentration as compared to the process stream. As noted above, rejection characteristics of suitable membranes with respect to shikimic acid are generally constant (e.g., about 70%). Thus, on an absolute mass basis of shikimic acid, contacting a suitable membrane with a process stream comprising a predefined mass of shikimic acid, regardless of the precise composition of the stream (e.g., concentration of shikimic acid), will typically result in rejection of a relatively constant proportion of shikimic acid. Thus, reference to depletion of the permeate with respect to shikimic acid indicates a lower mass of shikimic acid in the permeate as compared to the initial process stream. Accordingly, in various preferred embodiments (e.g., in which the shikimic acid is recovered from aqueous process streams produced by the plant method), a retentate is provided that is enriched in shikimic acid relative to the permeate. In various other preferred embodiments (e.g., in which the shikimic acid is produced by the fermentation method), a permeate enriched in shikimic acid relative to the retentate is provided.

Various preferred embodiments of the present invention include dilution prior to and/or diafilatration of the aqueous process stream during contact of the process stream and selective membrane. Diafiltration is a well-known technique in which a liquid stream (typically, but not limited to, demineralized water), is added to a feed stream introduced to a membrane separation unit to dilute the incoming feed. This dilution allows for additional permeate generation at a set pressure, due to a reduction in the feed stream's osmotic pressure. As additional permeate is generated, transmission of components through the nanofiltration membrane for which the membrane demonstrates a low rejection also increases. In this manner, diafiltration may preferably be employed to assist in the recovery and purification of a shikimic acid-containing aqueous process stream by taking advantage of the varying solute rejection characteristics demonstrated by suitable nanofiltration membranes.

For example, when the concentration of shikimic acid in the process stream is comparable to that of glyphosate and higher than the concentration of inorganic salts (e.g., a process stream provided by the fermentation method), diafiltration may be employed to increase the amount of shikimic acid that is transmitted through the nanofiltration membrane, due to the additional water transmission through the membrane. In this embodiment, as noted above, the permeate stream would contain the desired product shikimic acid. In addition, in accordance with these and various other embodiments in which the shikimic acid is produced by the fermentation method (e.g., those in which diafiltration is not utilized), a permeate is provided that is enriched in shikimic acid relative to the retentate.

By way of further example, when the concentration of shikimic acid in the shikimic acid-containing aqueous process stream is lower than the concentration of inorganic salts and significantly greater than the concentration of glyphosate (e.g., a process stream provided by the plant method), diafiltration may be employed to increase passage of inorganic salts through the nanofiltration membrane, due to the additional water transmission through the membrane and the relatively low rejection characteristic of the membrane with respect to the inorganic salts. In this embodiment, as noted above, the retentate stream would comprise the desired product shikimic acid and be enriched in shikimic acid relative to the permeate.

A. Recovery of Shikimic Acid Produced by the Plant Method

Figure 2:
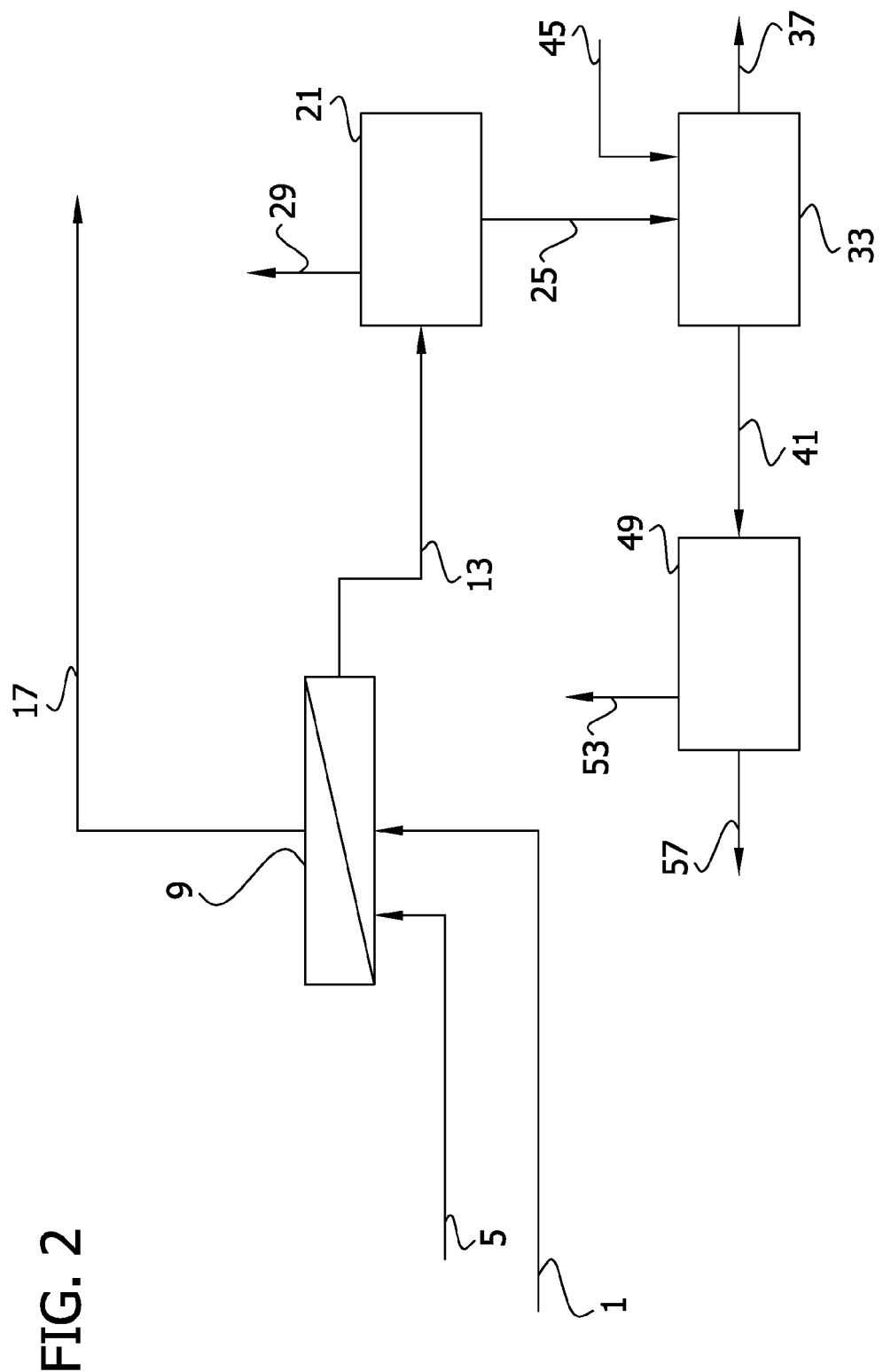
FIG. 2 is a schematic flowsheet of a process for recovering shikimic acid produced by the plant method.

FIG. 2 depicts one embodiment of a process for recovering and isolating shikimic acid from an aqueous process stream comprising a plant material extract prepared by the plant method as detailed elsewhere herein. As shown, an aqueous process stream 1 and optional dilution/diafiltration stream 5 are introduced into a membrane separation unit 9 containing a suitable separation membrane. Although shown in FIG. 2, dilution of the process stream (i.e., diafiltration) is not required for operation of the process depicted therein. Although not necessary, a plant extract may be concentrated prior to treatment for recovery and isolation of shikimic acid. Also not shown in FIG. 2 is an optional pH adjustment reagent stream for adjusting the pH of the aqueous process stream introduced into the membrane separation unit.

As detailed elsewhere herein, plants treated by contact with glyphosate may be harvested and treated for extraction of shikimic acid by methods that generally comprise subjecting plant material (e.g., roots, stalks, and leaves) to a washing operation followed by extraction of shikimic acid by methods known in the art including, for example, freeze thaw extraction using hydrochloric acid and solvent extraction using tridodecylamine. Preferably, the plant extract is prepared in the absence of organic solvents. Prior to the membrane separation operation, the aqueous plant extract may be subjected to a separation operation to remove plant material and produce a supernatant comprising shikimic acid (e.g., aqueous process stream 1 shown in FIG. 2). These processing steps are not shown in FIG. 2, but suitable apparatus and conditions may be readily selected by one skilled in the art generally and, more particularly, in view of the description of the "plant method" herein.

As shown in FIG. 2, contacting the aqueous process stream 1 and the separation membrane within membrane separation unit 9 forms a retentate 13 and a permeate 17. As detailed elsewhere herein, the permeate 17 is generally depleted in shikimic acid relative to the aqueous process stream and retentate, but does include a substantial fraction of inorganic salts, and is removed from the process as a waste stream.

However, as likewise described herein, the permeate does contain some shikimic acid. Thus, in accordance with various other embodiments, permeate 17 may be subjected to further membrane separation operations (e.g., recycled) for purposes of recovering shikimic acid therefrom. It is to be understood that any such treatment would generally be conducted in accordance with the discussion appearing herein. For example, the permeate may be treated in a further membrane separation unit as described below with reference to FIG. 3.

Nanofiltration is a pressure-driven separation process driven by the difference between the operating pressure and the osmotic pressure of the solution on the feed or retentate side of the membrane. The operating pressure in the membrane separation unit 9 will vary depending upon the type of membrane employed, as osmotic pressure is dependent upon the level of transmission of solutes through the membrane. Suitable operating pressures in membrane separation unit 9 (and any other membrane separation units utilized in accordance with the present invention) are achieved by passing the aqueous process stream 1 through one or more pumps (not shown) upstream of the membrane separation unit, for example, a combination booster pump and high-pressure pump arrangement.

Typically, the operating pressure utilized in nanofiltration operations is less than about 4500 kPa absolute and preferably from about 2000 to about 4000 kPa absolute. As illustrated in Example 12 below, a permeate flux of about 2 liters/minute/$m^2$ of membrane surface area can be achieved when treating a solution containing shikimic acid at an operating pressure of about 3500 kPa absolute.

In order to maintain or enhance membrane separation efficiency and permeate flux, the membranes should be periodically cleaned so as to remove contaminants from the surface of the membrane. Suitable cleaning includes cleaning-in-place (CIP) operations wherein the surface of the membrane is exposed to a cleaning solution while installed with membrane separation unit 9. Preferred systems monitor the component concentration of the retentate and/or permeate and/or the permeate flux to determine if cleaning is needed.

Cleaning protocols and cleaning solutions will vary depending on the type of separation membrane employed and are generally available from the membrane manufacturer. Suitable cleaning solutions may include, for example, caustic or alkaline solutions. In order to not damage the membranes and unnecessarily shorten membrane life, the CIP operation is preferably conducted using a solution of a standard pH at pressure and temperature conditions known to those skilled in the art. In some applications, it may be advantageous to conduct a cleaning operation on new separation membranes prior to use in the membrane separation operation in order to improve membrane performance.

Again with reference to FIG. 2, retentate 13 generally comprises shikimic acid, glyphosate, and various other impurities including, for example, various inorganic salts and ions thereof (e.g., phosphate ions, sulfate ions, potassium ions, chloride ions, and ammonium ions). These impurities may be provided by methods for producing shikimic acid by contacting a plant and glyphosate and/or may be native to the plants treated to prepare shikimic acid. As shown in FIG. 2, retentate 13 is transferred to a concentration vessel 21 wherein the retentate is treated to remove water and form a concentrated retentate 25 and aqueous waste stream 29. For example, water may be removed from the retentate 13 to provide concentrated retentate 25 by heating to evaporate a portion of the retentate water content. Removal of water from the retentate is currently believed to facilitate downstream recovery of desired shikimic acid product. Heating of the retentate for removal of water can be readily achieved by methods conventionally known in the art including, for example, indirect heat exchange with a suitable stream of fluid (e.g., a suitable heat transfer fluid such as steam). Heating of the retentate may also be suitably conduced by direct heating.

Again with reference to FIG. 2, concentrated retentate 25 is introduced into an ion exchange column or unit 33 containing a bed of ion exchange resin. The ion exchange resin is selected to be suitable for selective adsorption of glyphosate. The precise configuration of the ion exchange unit and composition of the ion exchange resin is not narrowly critical and may be selected in accordance with conventional methods utilizing apparatus and resins known in the art. For example, U.S. Pat. No. 5,087,740 to Smith, the entire contents of which are incorporated herein by reference for all relevant purposes, describes a method for separating glyphosate from an aqueous stream using a weakly basic ion exchange resin. Suitable ion exchange resins include those generally known in the art including, for example and without limitation, the weakly basic ion exchange resins sold by: Rohm & Haas Co. (Philadelphia, Pa.) under their Amberlite trademark such as AMBERLITE IRA-93, AMBERLITE IRA-94, AMBERLITE IRA-68 and AMBERLITE IRA-35; Diamond Shamrock Corp. (Dallas, Tex.) under their trademark DUOLITE A-392; and Sybron Chemicals, Inc. (Birmingham, N.J.) under their Ionac trademark such as IONAC 305, IONAC 365 and IONAC 380. Other suitable commercially available ion exchange resins can be readily selected by one skilled in the art.

As shown in FIG. 2, passing concentrated retentate 25 through the ion exchange unit 33 provides a waste stream 37 (upon regeneration) comprising glyphosate and an aqueous product solution 41 comprising desired product shikimic acid and depleted in glyphosate relative to the concentrated retentate by virtue of removal of glyphosate by ion exchange. It is currently believed that the separation of shikimic acid and glyphosate via ion exchange depicted in FIG. 2 provides near complete separation of glyphosate and shikimic acid and an aqueous product solution 41 containing no more than trace amounts of glyphosate.

Generally in accordance with the process shown in FIG. 2, as concentrated retentate 25 is passed through the ion exchange resin, more acidic glyphosate is selectively adsorbed by the resin while less acidic shikimic acid generally passes through the resin. Ion exchange separation is continued until passage or break-through of glyphosate through the ion exchange unit is detected, at which point the resin is washed and regenerated to produce waste stream 37 in accordance with conventional methods known in the art including suitable apparatus and process streams (not shown in FIG. 2).

Preparation of waste stream 37 comprising glyphosate generally includes selective adsorption and retention of glyphosate by the resin and generally further includes washing the resin by contact with a suitable aqueous washing liquid to remove glyphosate from the resin into the waste stream, and regenerate the resin. Waste stream 37 may be treated to recover glyphosate therefrom for use in various applications including, for example, the plant method detailed elsewhere herein.

Again with reference to FIG. 2, aqueous product solution 41 comprising desired product shikimic acid is transferred to a further concentration vessel 49 to reduce the water content of the product solution as described above to provide an aqueous waste stream 53 and a shikimic acid product 57. Preferably, the shikimic acid product has a moisture content of no more than about 20 wt %, more preferably no more than about 15 wt % and, still more preferably, no more than about 10 wt %.

FIG. 2 also shows pH adjustment stream 45 that is introduced into the ion exchange unit to provide conditions within the bed of ion exchange resin that are suitable for selective adsorption and retention of glyphosate and passage of shikimic acid therethrough. For example, to promote conditions suitable for retention of glyphosate, a relatively strong acid such as hydrochloric acid may be introduced to reduce and/or maintain the pH of the process stream below about 2 (e.g., from about 1 to about 2). In various alternative embodiments, recovery of shikimic acid may comprise selective adsorption and retention of shikimic acid in an ion exchange unit containing a bed of ion exchange resin selected for such purpose. Generally in accordance with such embodiments, the pH of the retentate contacted with the resin is higher (e.g., about 4) to promote retention of the shikimic acid by the ion exchange resin. Recovery of the shikimic acid retained by the ion exchange resin comprises regeneration of the ion exchange resin to remove the shikimic acid.

Multi-Pass Operation

Figure 3:
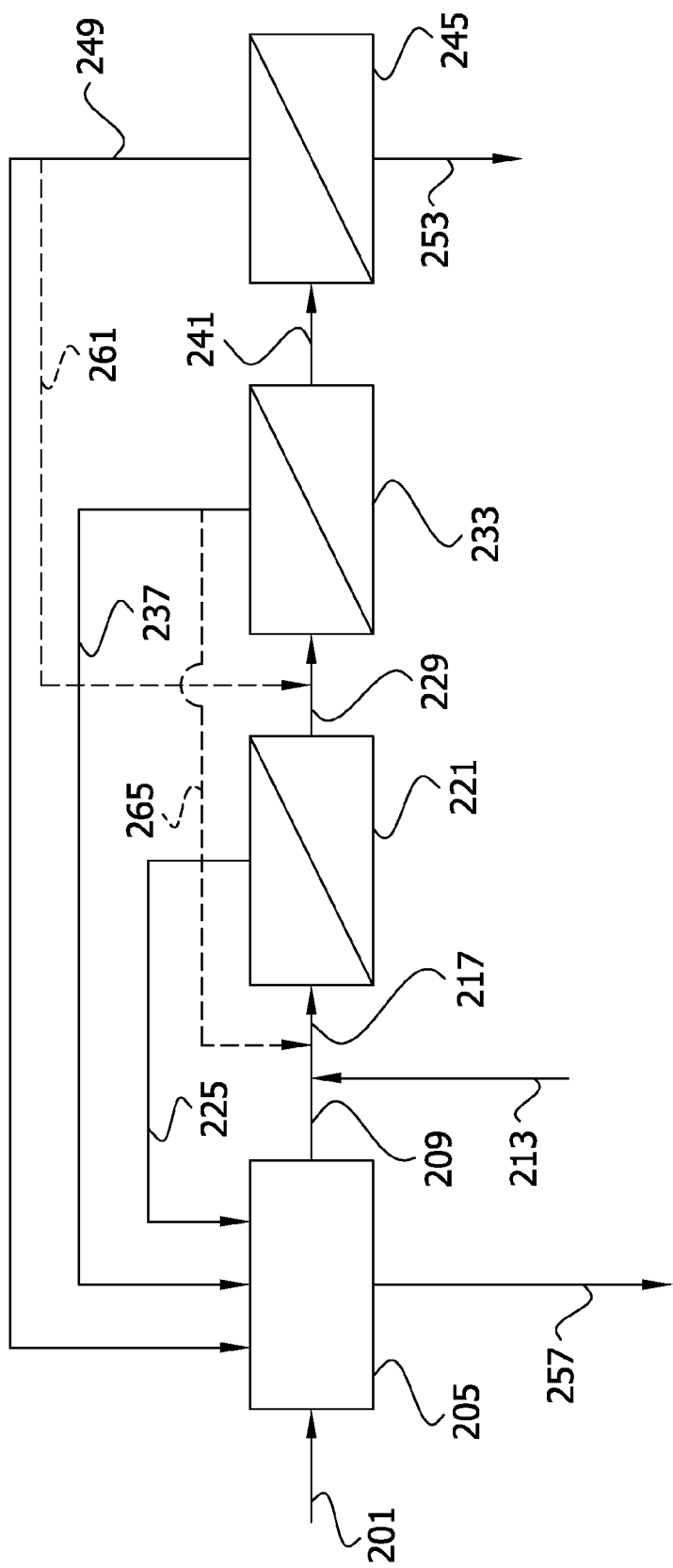
FIG. 3 is a schematic flowsheet of a multi-pass process for recovering shikimic acid produced by the plant method.

FIG. 3 depicts one embodiment of a multi-pass membrane separation process for recovering and isolating shikimic acid from an aqueous process stream comprising shikimic acid from plant material extract prepared by the plant method as detailed elsewhere herein. As shown in FIG. 3, plant extract effluent 201 is introduced into a plant extract storage tank 205. Plant extract feed 209 is removed from storage tank 205 and mixed with dilution stream 213 to form aqueous process stream 217. Aqueous process stream 217 is transferred to first membrane separation unit 221 and contacted with a first separation membrane to form a first retentate 225 and first permeate 229. As shown, first retentate 225 is returned to storage tank 205. In accordance with the foregoing discussion, first retentate 225 comprises shikimic acid. Accordingly, introduction of first retentate 225 into the storage tank enriches the shikimic acid content of the plant extract contained in the storage tank. Further in accordance with the foregoing discussion, first permeate 229 likewise comprises some shikimic acid. Accordingly, further treatment of first permeate 229 (as detailed below), allows for recovery of additional shikimic acid not recovered in first retentate 225.

First permeate 229 is introduced into second membrane separation unit 233 and contacted with a second nanofiltration separation membrane to form a second retentate 237 and second permeate 241. Second retentate 237 is returned to storage tank 205 and second permeate is transferred to third membrane separation unit 245 and contacted with a third nanofiltration separation membrane. As shown in FIG. 3, the effluents of third membrane separation unit 245 are third retentate 249 and waste stream 253. Third retentate 249 is returned to storage tank 205. FIG. 3 depicts the permeate from third membrane separation unit as a waste stream. It is to be understood that multi-pass membrane separation processes practiced in accordance with the present invention are not limited to utilizing three membrane separation units. Accordingly, stream 253 could be treated in a further membrane separation unit(s) for recovery of additional shikimic acid. Optionally (as shown by dashed lines 261 and 265 in FIG. 3), it is to be understood that retentates, in addition to being transferred to storage tank 205, may be recycled to upstream feed streams. For example, third retentate 249 may be introduced along with first permeate 229 into second membrane separation unit 233 as shown by dashed line 261. Similarly, second retentate 237 may be introduced along with stream 217 into first membrane separation unit 221 as shown by dashed line 265. It is to be further understood that a portion of a retentate may be introduced into storage tank 205 and a portion of the retentate may be recycled to an upstream feed stream as described above.

Combining first retentate 225, second retentate 237, and third retentate 249 returned to the storage tank provides enrichment of the plant extract with respect to shikimic acid content. Furthermore, contact of plant extract and the separation membrane(s) removes impurities (e.g., inorganic salts). Thus, introduction of one or more such retentates into the storage tank typically provides a reduction in impurity content of the plant extract contained therein. As shown in FIG. 3, a shikimic acid-enriched product stream 257 is removed from storage tank 205. This product stream may be treated in accordance with the above discussion for recovery of product shikimic acid therefrom including, for example, concentrating the product solution and separation from glyphosate by ion exchange.

B. Recovery of Shikimic Acid Produced from the Fermentation Method

Figure 4:
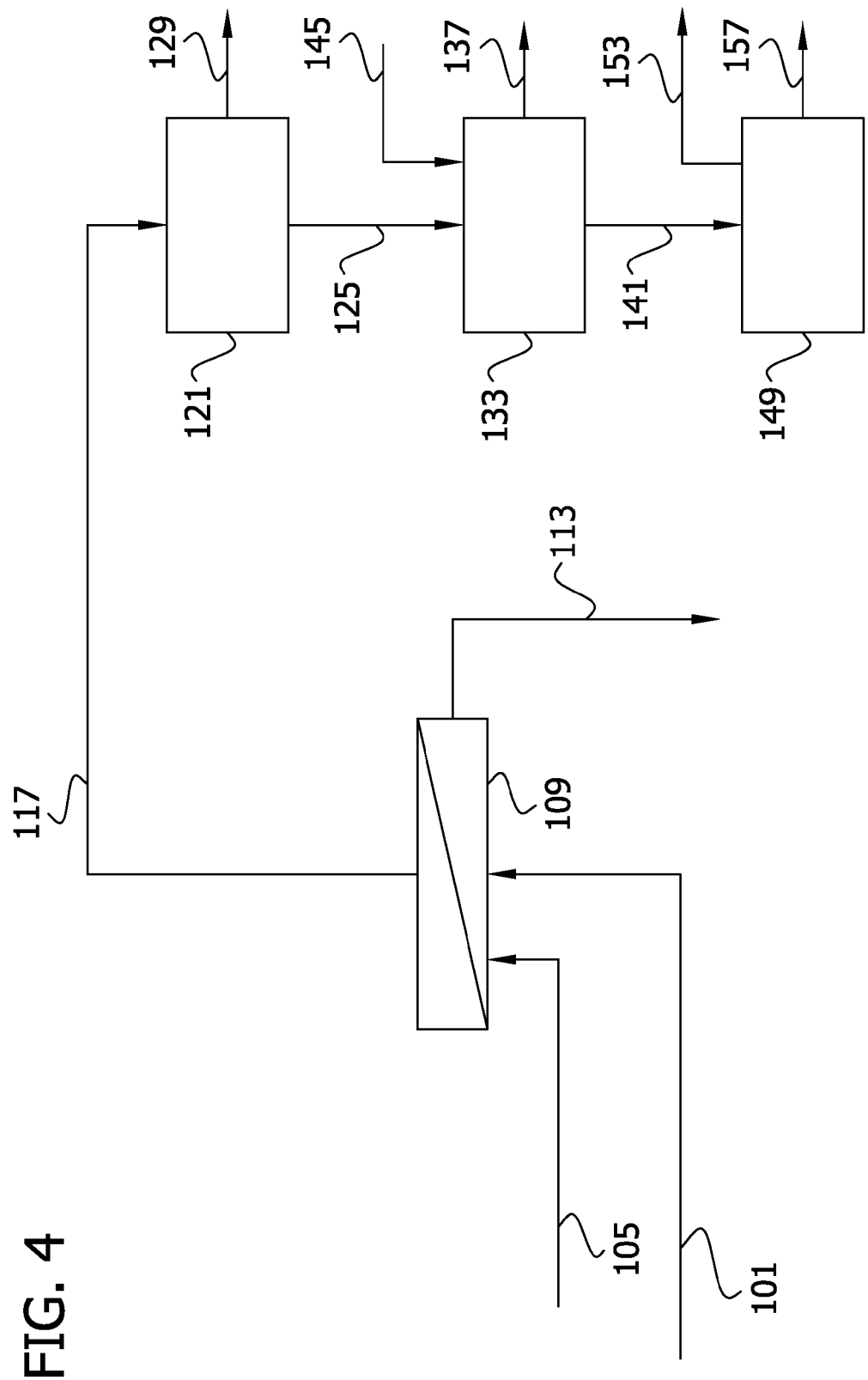
FIG. 4 is a schematic flowsheet of a process for recovering shikimic acid produced by the fermentation method.
Figure 5:
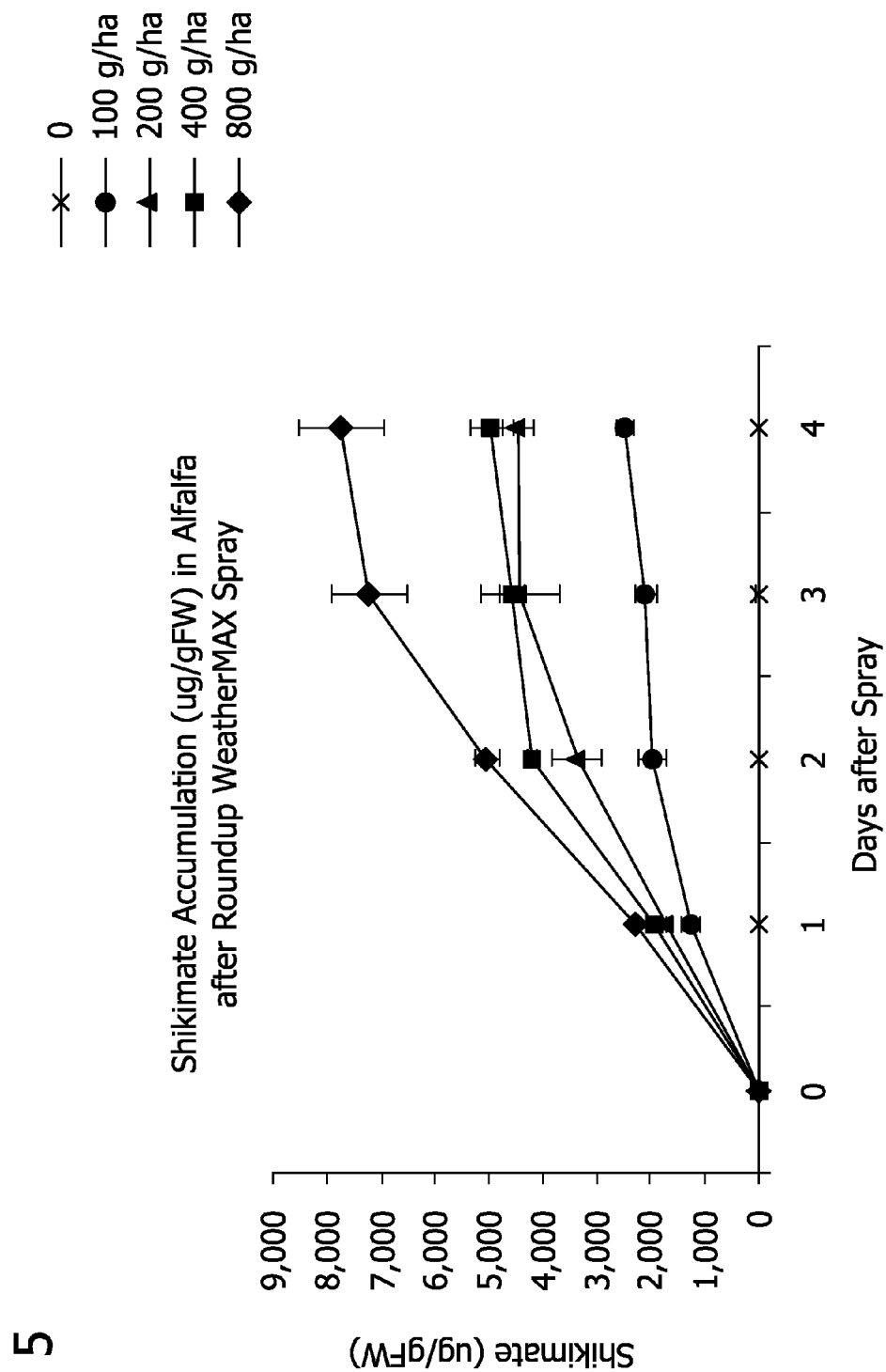
FIG. 5 shows shikimate accumulation in alfalfa after treatment with glyphosate as described in Example 1.

FIG. 4 depicts one embodiment of a method for recovering and isolating shikimic acid from an aqueous process stream comprising a cell culture medium or cell culture supernatant prepared by the fermentation method as detailed elsewhere herein. As shown, an aqueous process stream 101 and dilution/diafiltration stream 105 are introduced into a membrane separation unit 109 containing a suitable separation membrane. As noted above in connection with the process described in FIG. 2, diafiltration, when utilized, is generally conducted in accordance with conventional methods known in the art, but is not required. Similarly, an optional pH adjustment reagent stream for adjusting the pH of the aqueous process stream may be introduced into the aqueous process stream upstream of the membrane separation unit.

Aqueous process stream 101 generally comprises, or is in the form of a cell culture medium (fermentation broth) produced by the fermentation method detailed elsewhere herein. The fermentation broth containing shikimic acid may be subjected to a separation operation (e.g., centrifugation) and the resulting supernatant or centrate may be filtered to remove cellular debris. Although not necessary, a fermentation broth may be diluted by addition of an aqueous diluent (e.g., deionized water), or concentrated prior to treatment for recovery and isolation of shikimic acid.

As shown in FIG. 4, contacting the aqueous process stream 101 and the separation membrane within membrane separation unit 109 forms a retentate 113 and a permeate 117. Retentate 113 generally comprises glyphosate and various inorganic salts and ions thereof (e.g., phosphate ions, sulfate ions, potassium ions, chloride ions, and ammonium ions), and may be treated and the glyphosate recovered for use in, for example, the fermentation method detailed elsewhere herein. The retentate 113 also comprises some shikimic acid and, accordingly, may be subjected to further treatment in a multi-pass membrane separation process for further isolation of shikimic acid.

Permeate 117 generally comprises shikimic acid, phenylalanine, and various other impurities (e.g., potassium and sodium salts of phosphates, sulfates, and chlorides). As shown in FIG. 4, permeate 117 is transferred to a concentration vessel 121 to form a concentrated permeate 125 and an aqueous waste stream 129. Removal of water from permeate 117 to form concentrated permeate 125 may be readily conducted in accordance with methods known in the art including, for example, as described above in connection with FIG. 2.

Concentrated permeate 125 is introduced into an ion exchange column or unit 133 containing a bed of ion exchange resin selected to be suitable for selective adsorption and retention of phenylalanine. Suitable ion exchange resins include those generally known in the art including, for example, those described above. Generally in accordance with the process shown in FIG. 4, as concentrated permeate 125 is passed through the ion exchange resin, more acidic phenylalanine is selectively adsorbed by the resin while less acidic shikimic acid generally passes through the resin. Passage of concentrated permeate 125 through the ion exchange column continues until break-through of phenylalanine is detected, at which point the resin is washed and regenerated to produce waste stream 137.

As shown in FIG. 4, passing concentrated permeate 125 through ion exchange unit 133 provides an aqueous product solution 141 comprising desired product shikimic acid and depleted in phenylalanine relative to the permeate 117 and concentrated permeate 125. To provide advantageous conditions for separation of phenylalanine and shikimic acid, pH adjustment within the ion exchange unit 133 is provided by pH adjustment stream 145. To promote conditions suitable for retention of phenylalanine, a relatively strong acid such as hydrochloric acid may be introduced to reduce and/or maintain the pH of the process stream below about 2 (e.g., from about 1 to about 2) Waste stream 137 comprising phenylalanine is generally provided by washing the ion exchange resin with a suitable aqueous washing liquid. In addition to phenylalanine, the waste stream generally comprises one or more impurities including, for example, various salts such as potassium chloride and alkaline impurities such as ammonium hydroxide.

Again with reference to FIG. 4, aqueous product solution 141 comprising desired product shikimic acid is transferred to a further concentration vessel 149 to remove water from the product solution 141 as described above to provide an aqueous waste stream 153 and a shikimic acid product 157. Preferably, the shikimic acid product 157 has a moisture content of no more than about 20 wt. %, more preferably no more than about 15 wt. % and, still more preferably, no more than about 10 wt. %.

Although the preceding description focuses on the production, recovery, and isolation of shikimic acid, it should be understood that the methodology and techniques disclosed herein can be readily adapted by those skilled in the art for production, recovery and isolation of other cyclitolcarboxylic acids such as quinic acid.

Further in accordance with the present invention, various other embodiments are directed to methods for synthesizing a chemical compound, either in vitro or in vivo, wherein a cyclitolcarboxylic acid (e.g., shikimic acid or quinic acid) produced and/or recovered by any of the methods and processes detailed herein is used as a reagent in the synthesis. In preferred aspects of this embodiment of the invention, the compound is bioactive and has activity as an anti-microbial agent and/or a cell proliferation inhibitory agent (including, but not limited to a bioactive property selected from the group consisting of: anti-viral activity, anti-bacterial activity, anti-parasitical activity, or anti-cancer activity). In preferred aspects of this embodiment of the invention the compound has anti-bacterial and/or anti-viral properties. In some preferred embodiments, the invention provides a method for producing a neuraminidase inhibitor. In other aspects of this embodiment of the invention the synthesized compound is 6-fluoroshikimic acid or oseltamivir or oseltamivir phosphate prepared by any suitable method known to those skilled in the art.

In particular, neuraminidase inhibitors including oseltamivir can be produced by any method known in the art, including those described in International Patent Application Publication Nos. WO 07/080,321, WO 07/074,091, and U.S. Pat. Nos. 5,763,483; 5,866,601; 5,982,675; 6,593,314; 6,057,459; 6,111,132; 6,204,398; 6,225,341; 6,376,674; 6,518,438; 7,074,431; 6,939,986; and 6,437,171.

The chemical synthesis of oseltamivir from shikimic acid is further described in the scientific literature. See for example Rohloff et al. (1998) and Federspiel et al. (1999), among others. In preferred embodiments of the invention, the method yields at least about 1 kg of oseltamivir.

Having described the invention in detail, it will be apparent that modifications and variations are possible without departing from the scope of the invention defined in the appended claims.

EXAMPLES

The following examples are included to demonstrate preferred embodiments of the invention. It will be appreciated by those of skill in the art that the techniques disclosed in the following examples represent techniques discovered by the Applicants to function well in the practice of the invention, and thus can be considered to constitute preferred modes for its practice. However, those of skill in the art should, in light of the instant disclosure, also appreciate that many changes can be made in the specific embodiments that are disclosed, while still obtaining like or similar results, without departing from the scope of the invention. Thus, the examples are exemplary only and should not be construed to limit the invention in any way. To the extent necessary to enable and describe the instant invention, all references cited are herein incorporated by reference.

Plant Method

Example 1

Application, Harvest and Extraction of Shikimic Acid from Alfalfa

Alfalfa was established in a greenhouse in 4 inch pots and treated with glyphosate at an early vegetative stage. Approximately 8 plants per pot were treated at the V4 growth stage. Plants were treated with ROUNDUP WEATHERMAX in a track sprayer, at 0, 100, 200, 400 and 800 g a.e./ha and returned to the greenhouse. All treatments were replicated 5 times. Leaves were harvested at five time points: immediately after spray (t0), and at 1, 2, 3 and 4 days after treatment. After harvest, leaves were frozen on dry ice, weighed, and then stored at −80 C until extraction and analysis.

For t0 harvest, leaves were harvested immediately after treatment. For the 1, 2, 3 and 4 day harvest, plants were washed thoroughly with water from a spray hose and then allowed to dry before harvest. This procedure allowed for the measurement of the concentration of shikimic acid as well as an estimate of the concentration of glyphosate treatment (t0) and the amount of glyphosate absorbed and retained in treated leaves (1, 2, 3 and 4 days after treatment).

Shikimic Acid Extraction:

Leaf tissue was ground frozen on dry ice to a frozen powder. The entire t0 leaf samples were extracted directly in their 50 mL sampling tubes in 20 mL of 0.25 N HCl using a Polytron. The 50 mL tubes were centrifuged at 9500 rpm and 2 mL of supernatant was filtered through a 0.45 micron filter. For the shikimic acid analysis, 100 μL of filtrate was used. The 1, 2, 3 and 4 day samples were subsampled by transferring approximately 100 mg of frozen powder into tared 1.8 mL Sarstedt tubes and adding 900 μL of 0.25 N HCl. A stainless steel chip was added to each sample and the tubes were extracted by shaking on a Harbill paint shaker for 3 minutes. The tubes were centrifuged at 14,000 rpm and 100 μL of supernatant was used for shikimic acid analysis.

Extract Analysis:

For analysis, all extract samples were diluted 1:10 by adding 100 μL of sample supernatant or filtrate to 900 μL of 0.1% formic acid in an HPLC autosampler vial. An internal standard (100 μL, 238 μg/mL N-methyl glyphosate) was added to each of the diluted samples. All calibration standards were also prepared in a similar manner.

Extract analysis was performed using both HPLC/MS and HPLC/uv (210 nm) detection. Either 2 or 10 μL volumes of the diluted extracts were injected onto a Waters ZMD HPLC/MS system equipped with a 4.6 mm×250 mm, 5 micron ODS2 Waters Spherisorb® column (P/N PSS831915). Shikimic acid was also analyzed on a separate Agilent 1100 HPLC system equipped with a 4.6 mm×250 mm, 5 micron ODS2 Waters Spherisorb® column (P/N PSS831915) using a photodiode array detector.

Results are shown in FIG. 5. As has clearly been demonstrated, shikimic acid accumulates to significantly high levels in alfalfa over time after treatment with glyphosate. Furthermore, the rate of shikimic acid accumulation is related to the rate of glyphosate applied.

The shikimic acid produced and extracted by the above method is purified and the final product is used as a raw material in the production of a neuraminidase inhibitor using methods known in the art.

Example 2

Application, Harvest and Extraction of Shikimic Acid from Soybean

Soybean plants were established in a greenhouse in 4 inch pots and treated with glyphosate at an early vegetative stage. Approximately 1 plant per pot was treated at the V2 growth stage. Plants were treated with ROUNDUP WEATHERMAX in a track sprayer, at 0, 100, 200, 400 and 800 g a.e./ha and returned to the greenhouse. All treatments were replicated 5 times. Leaves were harvested at five time points: immediately after spray (t0), and at 1, 2, 3 and 4 days after treatment. After harvest, leaves were frozen on dry ice, weighed, and then stored at −80 C until extraction and analysis.

For t0 harvest, leaves were harvested immediately after treatment. For the 1, 2, 3 and 4 day harvest, plants were washed thoroughly with water from a spray hose and then allowed to dry before harvest. This procedure allowed for the measurement of the concentration of shikimic acid as well as an estimate of the concentration of glyphosate treatment (t0) and the amount of glyphosate absorbed and retained in treated leaves (1, 2, 3 and 4 days after treatment).

Shikimic Acid Extraction:

Leaf tissue was ground frozen on dry ice to a frozen powder. The entire t0 leaf samples were extracted directly in their 50 mL sampling tubes in 20 mL of 0.25 N HCl using a Polytron. The 50 mL tubes were centrifuged at 9500 rpm and 2 mL of supernatant was filtered through a 0.45 micron filter. For the shikimic acid analysis, 100 μL of filtrate was used. The 1, 2, 3 and 4 day samples were subsampled by transferring approximately 100 mg of frozen powder into tared 1.8 mL Sarstedt tubes and adding 900 μL of 0.25 N HCl. A stainless steel chip was added to each sample and the tubes were extracted by shaking on a Harbill paint shaker for 3 minutes. The tubes were centrifuged at 14,000 rpm and 100 μL of supernatant was used for shikimic acid analysis.

Extract Analysis:

For analysis, all extract samples were diluted 1:10 by adding 100 μL of sample supernatant or filtrate to 900 μL of 0.1% formic acid in an HPLC autosampler vial. An internal standard (100 μL, 238 μg/mL N-methyl glyphosate) was added to each of the diluted samples. All calibration standards were also prepared in a similar manner.

Extract analysis was performed using both HPLC/MS and HPLC/uv (210 nm) detection. Either 2 or 10 μL volumes of the diluted extracts were injected onto a Waters ZMD HPLC/MS system equipped with a 4.6 mm×250 mm, 5 micron ODS2 Waters Spherisorb® column (P/N PSS831915). Shikimic acid was also analyzed on a separate Agilent 1100 HPLC system equipped with a 4.6 mm×250 mm, 5 micron ODS2 Waters Spherisorb® column (P/N PSS831915) using a photodiode array detector.

Figure 6:
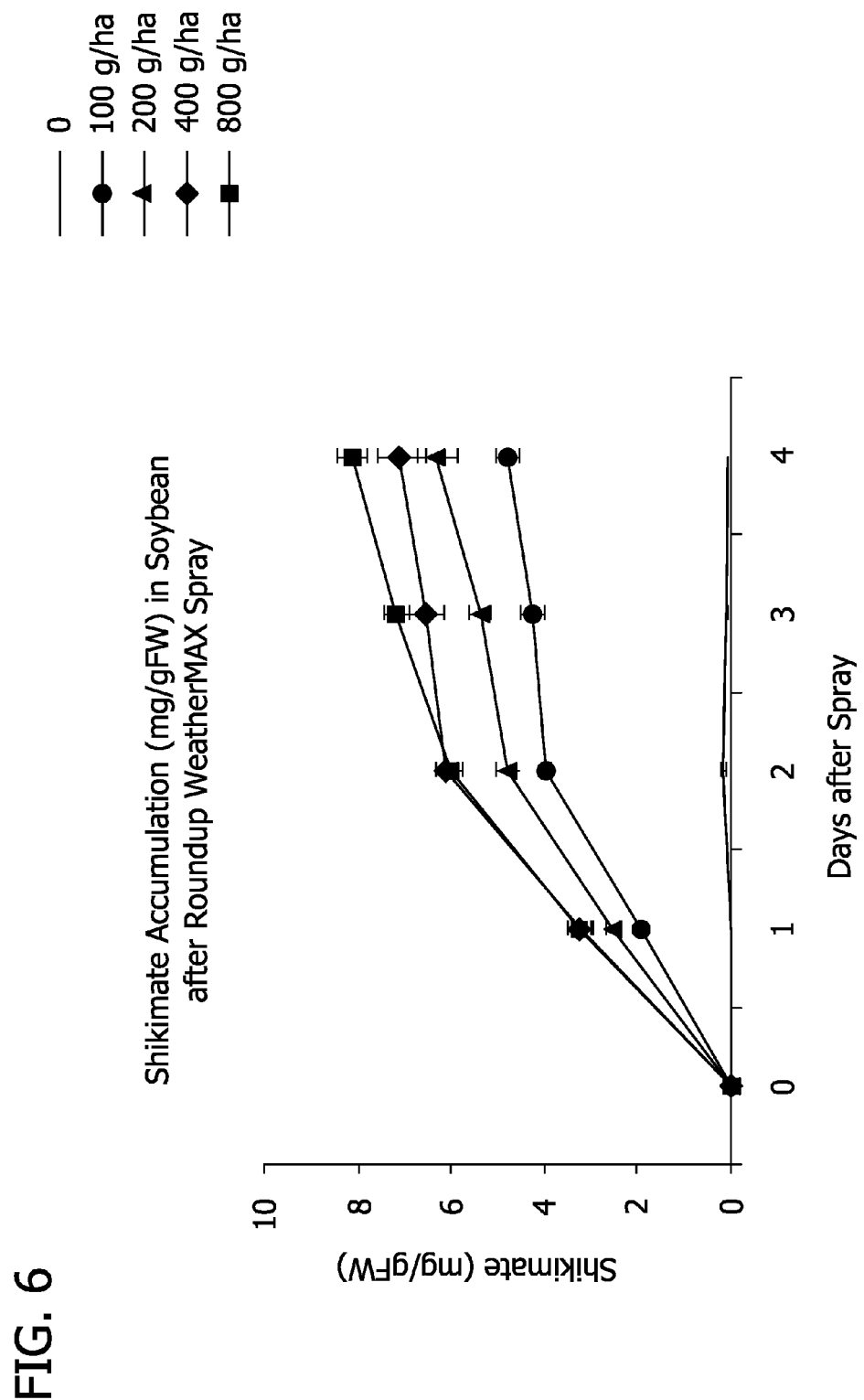
FIG. 6 shows shikimate accumulation in soybean after treatment with glyphosate as described in Example 2.

Results of this experiment are shown in FIG. 6. As has clearly been demonstrated, shikimic acid accumulates to significantly high levels in soybean after treatment with glyphosate. Furthermore, the rate of shikimic acid accumulation is related to the rate of glyphosate applied.

Example 3

Shikimic Acid Yield from Various Plant Species

Plant species including soybean, alfalfa, wheat, annual ryegrass, perennial ryegrass, sunflower, and sugar beet were evaluated to determine the yield of shikimic acid resulting from treatment with ROUNDUP Herbicide.

Plants were treated with ROUNDUP WEATHERMAX in a track sprayer at 800 g a.e./ha and returned to the greenhouse. All treatments were replicated 5 times. Leaves were harvested at three days after treatment. After harvest, leaves were frozen on dry ice, weighed, and then stored at −80° C. until extraction and analysis.

Shikimic Acid Extraction:

Leaf tissue was ground frozen on dry ice to a frozen powder. The frozen powder was stored in sample tubes for subsequent subsampling and extraction. Approximately 100 mg of frozen powder was weighed into tared 1.8 mL Sarstedt tubes and extracted into 900 μl of 0.25 N HCl. A stainless steel chip was added to each sample and the tubes were extracted by shaking on a Harbill paint shaker for 3 minutes. The tubes were centrifuged at 14,000 rpm and the supernatant was used for HPLC analysis.

Extract Analysis:

For analysis, plant extract samples were diluted 1:10 by removing 100 μL from a sample supernatant vial and diluting with 900 μL of 0.1% formic acid in an HPLC autosampler vial. An internal standard (100 μL, 238 μg/mL N-methyl glyphosate) was added to each of the diluted samples. All calibration standards were also prepared in a similar manner.

Extract analysis was performed using both HPLC/MS and HPLC/uv (210 nm) detection. Either 2 or 10 μL volumes of the diluted extracts were injected onto a Waters ZMD HPLC/MS system equipped with a 4.6 mm×250 mm, 5 micron ODS2 Waters Spherisorb® column (P/N PSS831915). Shikimic acid was also analyzed on a separate Agilent 1100 HPLC system equipped with a 4.6 mm×250 mm, 5 micron ODS2 Waters Spherisorb® column (P/N PSS831915) using a photodiode array detector. Results from this experiment are shown in Table 1 below:

TABLE 1

Shikimic acid accumulation (mg/g FW) in leaves of plants sprayed with ROUNDUP WEATHERMAX, harvested 3 days after treatment.

| Plant Species | Untreated Control | Treated (800 g/ha) |
|---|---|---|
| Soybean | 0.1 | 7.2 |
| Alfalfa | 0.0 | 7.2 |
| Wheat | 0.0 | 2.3 |
| Annual Ryegrass | 0.6 | 3.5 |
| Perennial Ryegrass | 0.4 | 2.4 |
| Sunflower | 0.0 | 2.6 |
| Sugar beet | 0.0 | 0.6 |

Example 4

Quinic Acid Yield from Various Plant Species

During the same experiment described in Example 3, plant species including soybean, alfalfa, wheat, annual ryegrass, perennial ryegrass, sunflower, and sugar beet were also evaluated to determine the yield of quinic acid. The analysis of quinic acid was performed on the plant extracts samples containing the shikimic acid by means of the analytical methodology utilized for the shikimic acid determination. Results from this experiment are shown in Table 2 below.

TABLE 2

Quinic acid accumulation (mg/g FW) in leaves of plants sprayed with ROUNDUP WEATHERMAX, harvested 3 days after treatment.

| Plant Species | Untreated Control | Treated (800 g/ha) |
|---|---|---|
| Soybean | 0.00 | 0.00 |
| Alfalfa | 0.00 | 0.00 |
| Wheat | 0.38 | 1.2 |
| Annual Ryegrass | 0.84 | 2.3 |
| Perennial Ryegrass | 1.39 | 5.6 |
| Sunflower | 0.08 | 1.5 |
| Sugar beet | 0.00 | 0.01 |

Fermentation Method

Example 5

Construction of a pBR322-Derived Plasmid Expressing an Unregulated pheA Gene Encoding a Chorismate Mutase-Prephenate Dehydratase Enzyme that is Resistant to Feedback-Inhibition by Phenylalanine A pheA gene with three alterations in the nucleotide sequence was prepared by DNA synthesis as an EcoRI-BamHI restriction fragment (SEQ ID NO: 1). The technique of DNA synthesis is known in the art (Khudyakov and Fields, 2003).

The three alterations were:
1. A promoter-up mutation in the −10 region of the pheA promoter, changing it from TACTGTA to TATAATA (FIG. 7).
2. A 146 bp deletion between the pheA promoter and the ribosome binding site (RBS) of the pheA gene, removing the pheA attenuator region including the pheL leader peptide gene (FIG. 7)

3. A 6 bp deletion spanning codons 304-305-306 of the pheA gene, altering the amino acid sequence of the encoded chorismate mutase-prephenate dehydratase from Ala-303, Thr-304, Gly-305, Gln-306, Gln-307 to Ala-Lys-Gln (SEQ ID NO:2). The nucleotide sequence (SEQ ID NO: 1) is changed from GCG-A<u>CC-GGG-C</u>AA-CAA to GCG-AAA-CAA; the 6 bp deletion is of the underlined nucleotides CC-GGG-C.

All three of these alterations to the nucleotide sequence of the pheA gene are known in the art (Nelms et al., 1992; Fotheringham and Nelms, U.S. Pat. No. 5,120,837; Fotheringham and Nelms, European Patent EP 0418840 B1). The change from TACTGTA to TATAATA (SEQ ID NO: 4) in the promoter region of the pheA gene (FIG. 7) increases the activity of this promoter. Removal of the pheA attenuator region including the pheL leader peptide gene (FIG. 7) leads to constitutive expression of the pheA gene, no longer subject to an attenuation mechanism of repression by phenylalanine (Pittard, 1996). The changes in the amino acid sequence of the altered chorismate mutase-prephenate dehydratase (SEQ ID NO:2) result in the enzyme being resistant to feedback-inhibition by phenylalanine.

This synthetic EcoRI-BamHI restriction fragment, carrying the altered pheA gene, was inserted into the standard cloning vector pBR322 (Bolivar et al, 1977; Pouwels et al., 1985; Balbas et al., 1986; Balbas et al., 1988) to yield the plasmid pXT1457. The techniques of manipulation of DNA molecules, including the cleavage of DNA molecules with restriction enzymes and the ligation of restriction fragments of DNA, are known in the art (Sambrook and Russell, 2001; Ausubel et al., 2005). While the plasmid pBR322 encodes resistance to both ampicillin and tetracycline, insertion of a DNA fragment between the EcoRI and BamHI sites of pBR322 disrupts the tetracycline resistance gene, and so pXT1457 encodes resistance only to ampicillin.

To confirm that the new plasmid was functioning as expected, the wild-type *E. coli* K-12 host strain LBB427 was transformed with the plasmid pXT1457. Techniques for transforming bacteria, including strains of *E. coli*, are known in the art (Sambrook and Russell, 2001; Ausubel et al., 2005). The shikimic acid and phenylalanine production levels of this strain were compared to that of the untransformed host strain LBB427. The strains were cultured in 50 milliliters of Vogel-Bonner minimal culture medium (Vogel and Bonner, 1956), consisting of magnesium sulfate heptahydrate ($MgSO_4$-$7H_2O$) at 298 milligrams per liter, anhydrous dibasic potassium phosphate ($K_2HPO_4$) at 14.93 grams per liter, sodium ammonium phosphate tetrahydrate ($NaNH_4HPO_4$-$4H_2O$) at 5.22 grams per liter, anhydrous citric acid (the free acid form) at 2.73 grams per liter, and glucose at 2.00 grams per liter. The pH of the culture medium was 7.0. For the strain LBB427 transformed with the plasmid pXT1457, ampicillin was included in the culture medium at 100 milligrams per liter. The cultures were grown in flasks, on an incubator shaker operating at 300 rpm and 37 degrees Celsius. At 24 hours after inoculation, the cells were pelleted by centrifugation, and the culture supernatants were analyzed by a high-pressure liquid chromatography (HPLC) assay for shikimic acid and phenylalanine content. To the samples to be assayed, phosphoric acid was added to a final concentration of 6 millimolar. The samples were injected onto a 0.5 centimeter by 200 centimeter Altec 5 micron Bondapak C-18 column, and the eluate was scanned from 190 to 300 nanometers.

Under these growth conditions, while the untransformed host strain LBB427 did not produce detectable levels of phenylalanine in the culture supernatant, the host strain LBB427 transformed with the plasmid pXT1457 did produce phenylalanine in the culture supernatant, at levels of about 400 milligrams of phenylalanine per optical density (OD) unit per liter.

Under these growth conditions, the untransformed host strain LBB427 did not produce detectable levels of shikimic acid in the culture supernatant. The host strain LBB427 transformed with the plasmid pXT1457 did produce shikimic acid in the culture supernatant, at levels of about 3 milligrams of shikimic acid per OD unit per liter.

These results confirmed that the presence of the altered pheA gene on the pBR322-derived plasmid pXT1457 transformed into the host strain LBB427 was leading to a deregulation of the common aromatic biosynthetic pathway in the strain.

Example 6

Construction of a pSC101-Derived Plasmid Expressing an Unregulated pheA Gene Encoding a Chorismate Mutase-Prephenate Dehydratase Enzyme that is Resistant to Feedback-Inhibition by Phenylalanine Plasmids derived from pBR322, such as pXT1457 described in Example 5, exist in an *E. coli* host cell at a copy number (the number of plasmid molecules per cell) of about 30; this copy number determination is described in Bogosian et al., International Publication No. WO 2007/035323 A1, which is hereby incorporated herein by reference in its entirety. To investigate the effect of the altered pheA gene when present on a lower copy number plasmid vector, a pSC101-derived cloning vector was constructed. The plasmid pSC101 has a copy number of about 15 (Hasunuma and Sekiguchi, 1977), which is intermediate between that of low copy number plasmids and high-copy number plasmids such as pBR322 (Armstrong et al., 1984).

The starting plasmid was the cloning vector pXT995. The plasmid pXT995 and its construction are described in Bogosian et al., International Publication No. WO 2007/035323 A1, which is hereby incorporated herein by reference in its entirety. The plasmid pXT995 is essentially the plasmid pBR322, with the only difference being that the pBR322-derived origin of replication on pXT995 is flanked by arrays of convenient restriction sites. At one end of the origin of replication, the array of restriction sites includes a site for the restriction enzyme NsiI, and at the other end of the origin of replication, the array of restriction sites includes a site for the restriction enzyme SacI. Thus, the origin of replication on the plasmid pXT995 can be excised by digestion of the plasmid with the enzymes NsiI and SacI, and replaced with an NsiI-SacI restriction fragment carrying a different origin of replication.

The origin of replication of the plasmid pSC101 was amplified by the polymerase chain reaction as an NsiI-SacI restriction fragment, and inserted into the plasmid pXT995. The technique of amplifying segments of DNA by the polymerase chain reaction is known in the art (Sambrook and Russell, 2001; Ausubel et al., 2005). This insertion replaced the NsiI-SacI fragment on pXT995 (that carried the pBR322-derived origin of replication) with the pSC101-derived origin of replication. The resulting plasmid was designated pXT1405. The plasmid pXT1405 is thus composed of the backbone of pBR322, including the genes encoding resistance to ampicillin and tetracycline, but with an origin of replication from pSC101.

This EcoRI-BamHI restriction fragment from pXT1457 (described in Example 5), carrying the altered pheA gene, was inserted into this new cloning vector pXT1405 to yield the plasmid pXT1483 (SEQ ID NO: 3). While the plasmid pXT1405 encodes resistance to both ampicillin and tetracycline, insertion of a DNA fragment between the EcoRI and BamHI sites of pXT1405 disrupts the tetracycline resistance gene, and so pXT1483 encodes resistance only to ampicillin.

Example 7

Treatment of Strains with Glyphosate

The untransformed host strain LBB427 and the host strain LBB427 transformed with the plasmid pXT1457 were grown in 50 milliliters of the Vogel-Bonner minimal culture medium described in Example 5. For the strain LBB427 transformed with the plasmid pXT1457, ampicillin was included in the culture medium at 100 milligrams per liter. The cultures were grown in flasks, on an incubator shaker operating at 300 rpm and 37 degrees Celsius. At 2.5 hours after inoculation, N-(phosphonomethyl)glycine was added to a concentration of 3.38 grams per liter (20 millimolar). Growth of the cultures was almost completely inhibited by this level of glyphosate. At 24 hours after inoculation (i.e., 21.5 hours after N-(phosphonomethyl)glycine addition), the cells were pelleted by centrifugation, and the culture supernatants were analyzed for shikimic acid content using the HPLC assay described in Example 5. The culture supernatants of the host strain LBB427 transformed with the plasmid pXT1457 were also analyzed for phenylalanine content.

Under these conditions of glyphosate treatment, the untransformed host strain LBB427 did not produce detectable levels of shikimic acid in the culture supernatant.

Under these same conditions of glyphosate treatment, the host strain LBB427 transformed with the plasmid pXT1457 also did not produce detectable levels of shikimic acid in the culture supernatant. This strain did produce phenylalanine in the culture supernatant, but only at levels of about 50 milligrams of phenylalanine per OD unit per liter.

These results indicated that the inhibition of the enzyme EPSP synthase by glyphosate inhibited the growth of both the transformed and untransformed strains, and reduced the biosynthesis of phenylalanine by the strain LBB427 transformed with the plasmid pXT1457. The fact that both the transformed and the untransformed strains did not produce detectable levels of shikimic acid indicated that the inhibition of the enzyme EPSP synthase by glyphosate was causing shikimate-3-phosphate to accumulate rather than shikimic acid.

Example 8

Growth of Strains Under Phosphate-Limiting Conditions

A phosphate-limiting culture medium was developed by the Applicants, containing anhydrous magnesium sulfate ($MgSO_4$) at 192 milligrams per liter, ammonium chloride ($NH_4Cl$) at 5.35 grams per liter, potassium chloride (KCl) at 3.73 grams per liter, sodium chloride (NaCl) at 1.17 grams per liter, triethanolamine (a buffering compound) at 22.3 grams per liter, and glucose at 1.5 grams per liter. The pH of the culture medium was 7.0. This culture medium does not contain any source of phosphate. This culture medium was designated PF culture medium (standing for phosphate-free culture medium). However, a phosphate-limiting medium may be formulated for use in the present invention such that, while not phosphate-free, it contains minimal amounts of phosphate (i.e., is substantially free of phosphate). Such a medium will create the phosphate-limiting conditions that result in a yield of shikimic acid in the cultured microorganisms that is comparable to the yield achieved when using a phosphate-free medium and that is greater than the yield achieved when using a typical phosphate containing medium such as the Vogel-Bonner minimal culture medium disclosed in Example 5. Generally, such a phosphate-limiting medium should contain phosphate at levels no more than about 1 millimolar, and preferably at levels no more than about 100 micromolar.

For pre-growth of the strains, sources of phosphate were supplied to this culture medium in the form of Casamino acids at 2.2 grams per liter and yeast extract at 300 milligrams per liter. This culture medium was designated PF-CAA/YE culture medium (standing for PF culture medium plus Casamino acids and yeast extract).

The untransformed host strain LBB427 and the host strain LBB427 transformed with the plasmid pXT1457 were grown initially in 50 milliliters of the PF-CAA/YE culture medium. For the strain LBB427 transformed with the plasmid pXT1457, ampicillin was included in the culture medium at 100 milligrams per liter. The cultures were grown for 2.5 hours in flasks, on an incubator shaker operating at 300 rpm and 37 degrees Celsius. The cells in these cultures were pelleted by centrifugation and resuspended in the same volume of the PF culture medium. For the strain LBB427 transformed with the plasmid pXT1457, ampicillin was included in the culture medium at 100 milligrams per liter. Upon return to the incubator shaker, the strains exhibited very little additional growth, confirming that they were phosphate-limited. The small amount of additional growth that was observed was presumably due to carry-over of small amounts of phosphate, most likely in the form of phosphate reserves inside the cells themselves. At 24 hours after inoculation, the cells were pelleted by centrifugation, and the culture supernatants were analyzed for shikimic acid content using the HPLC assay described in Example 5. The culture supernatants of the host strain LBB427 transformed with the plasmid pXT1457 were also analyzed for phenylalanine content.

Under these conditions of phosphate limitation, the untransformed host strain LBB427 did not produce detectable levels of shikimic acid in the culture supernatant. Under these same conditions of phosphate limitation, the host strain LBB427 transformed with the plasmid pXT1457 also did not produce detectable levels of shikimic acid in the culture supernatant. This strain did produce phenylalanine in the culture supernatant, at levels of about 500 milligrams of phenylalanine per OD unit per liter.

These results indicated that phosphate limitation of either the transformed or the untransformed strains did not lead to production of shikimic acid.

Example 9

Growth of Strains Under Phosphate-Limiting Conditions Combined with Treatment with Glyphosate The untransformed host strain LBB427 and the host strain LBB427 transformed with the plasmid pXT1457 or with the plasmid pXT1483 were grown initially in 50 milliliters of the PF-CAA/YE culture medium described in Example 8. For the strains of LBB427 transformed with the plasmid pXT1457 or with the plasmid pXT1483, ampicillin was included in the culture medium at 100 milligrams per liter. The cultures were grown for 2.5 hours in flasks, on an incubator shaker operating at 300 rpm and 37 degrees Celsius. The cells in these cultures were pelleted by centrifugation and resuspended in the same volume of the PF culture medium described in Example 8. For the strains of LBB427 transformed with the plasmid pXT1457 or with the plasmid pXT1483, ampicillin was included in the culture medium at 100 milligrams per liter. To these resuspended cultures, N-(phosphonomethyl) glycine was added to a concentration of 3.38 grams per liter (20 millimolar). Upon return to the incubator shaker, the strains exhibited very little additional growth. At 24 hours after inoculation (i.e., 21.5 hours after N-(phosphonomethyl) glycine addition), the cells were pelleted by centrifugation, and the culture supernatants were analyzed for shikimic acid content using the HPLC assay described in Example 5.

Under these conditions of glyphosate treatment and phosphate-limitation, the untransformed host strain LBB427 produced shikimic acid in the culture supernatant at levels of about 200 milligrams of shikimic acid per OD unit per liter. The host strain LBB427 transformed with the plasmid pXT1457 produced shikimic acid in the culture supernatant at levels of about 250 milligrams of shikimic acid per OD unit per liter. The host strain LBB427 transformed with the plasmid pXT1483 produced shikimic acid in the culture supernatant at levels of about 400 milligrams of shikimic acid per OD unit per liter.

It is possible that not all of the accumulated shikimate-3-phosphate in these cells had been converted into shikimic acid and excreted into the culture medium. As noted above, it has been reported that shikimate-3-phosphate can be converted to shikimic acid by lowering the pH and/or raising the temperature of culture samples (Davis and Mingioli, 1953). A sample of the culture of the host strain LBB427 transformed with the plasmid pXT1483 (taken at 24 hours after inoculation), including the cells, was adjusted to pH 1.0 with sulfuric acid, and heated to 60 degrees Celsius for 15 minutes. The cells were pelleted by centrifugation, and the culture supernatant was analyzed for shikimic acid content using the HPLC assay described in Example 5. The level of shikimic acid was found to be about 600 milligrams per OD unit per liter.

These results indicated that with the untransformed host strain LBB427, the inhibition of the enzyme EPSP synthase by glyphosate, combined with induction of the enzyme alkaline phosphatase by phosphate limitation, caused the strain to produce and excrete into the culture medium substantial quantities of shikimic acid.

These results further demonstrated that with the host strain LBB427 transformed with the plasmid pXT1457 or with the plasmid pXT1483, the combination of deregulation of the common aromatic biosynthetic pathway, glyphosate inhibition of the enzyme EPSP synthase, and induction of the enzyme alkaline phosphatase by phosphate limitation, caused the strain to produce and excrete into the culture medium even higher quantities of shikimic acid. Additional shikimic acid could be recovered from these cells by lowering the pH and raising the temperature of culture samples.

While not wishing to be bound by theory, the higher yield of shikimic acid obtained with the host strain LBB427 transformed with the plasmid pXT1483, compared to the host strain LBB427 transformed with the plasmid pXT1457, is possibly due to the lower plasmid copy number of pXT1483. The metabolic burden on cells to maintain multicopy plasmids is significant (Bentley et al., 1990), and could affect the capacity of the cell to produce compounds such as shikimic acid.

Example 10

Production of Shikimic Acid from a High-Density Fermentation Culture

The host strain LBB427 transformed with the plasmid pXT1483 can be grown to high optical densities in a phosphate-limited fermentation culture. Fermentations are conducted in a chemically-defined minimal medium containing 5.9 grams of anhydrous ammonium sulfate (($NH_4)_2SO_4$), 1.8 grams of anhydrous dibasic potassium phosphate ($K_2HPO_4$), 1.0 grams of monobasic sodium phosphate monohydrate ($NaH_2PO_4$—$H_2O$), 550 milligrams of magnesium sulfate heptahydrate ($MgSO_4$-$7H_2O$), 27 milligrams of ferric chloride hexahydrate ($FeCl_3$-$6H_2O$), 0.5 milligrams of zinc sulfate heptahydrate ($ZnSO_4$-$7H_2O$), 0.9 milligrams of cobalt chloride hexahydrate ($CoCl_2$-$6H_2O$), 0.9 milligrams of sodium molybdate dihydrate ($Na_2MoO_4$-$2H_2O$), 1.1 milligrams of cupric sulfate pentahydrate ($CuSO_4$-$5H_2O$), 0.3 milligrams of boric acid ($H_3BO_3$), and 0.7 milligrams of manganese sulfate monohydrate ($MnSO_4$—$H_2O$) per liter of water. The fermenter is maintained at 37 degrees Celsius. The pH is maintained at 7.0 by the controlled addition of concentrated (about 29%) ammonium hydroxide ($NH_4OH$). Glucose is fed at a controlled rate from a 50% stock solution to maintain a glucose concentration of 0.2%.

In the presence of excess phosphate, such fermentation cultures can be grown to optical densities in excess of 50 or even higher. In this phosphate-limited fermentation culture medium, the onset of phosphate starvation is apparent when the growth of the culture stops at lower optical densities. The addition of a small amount of additional phosphate, fed from a stock solution of 85% phosphoric acid ($H_3PO_4$), would allow the strain to grow to a higher optical density. When the culture reaches an optical density of about 20-40, and phosphate starvation has been initiated, N-(phosphonomethyl) glycine is added to a final concentration of 3.38 grams per liter (20 millimolar).

Twelve hours after N-(phosphonomethyl)glycine addition, samples of the fermentation cultures are taken for analysis of shikimic acid levels. The samples, including the cells, are adjusted to pH 1.0 with sulfuric acid, and heated to 60 degrees Celsius for 15 minutes. The cells are pelleted by centrifugation, and the culture supernatants are analyzed for shikimic acid content using the HPLC assay described in Example 5.

At an optical density of 40, shikimic acid is produced in the culture supernatant at levels of about 24 grams of shikimic acid per liter.

Example 11

Recovery and Isolation/Purification of Shikimic Acid from Culture Medium

Shikimic acid was recovered from the culture medium of the untransformed host strain LBB427 and the host strain LBB427 transformed with the plasmid pXT1457 or with the plasmid pXT1483, grown under phosphate-limiting conditions and treated with N-(phosphonomethyl)glycine as described in Example 9.

The cells in the cultures were pelleted by centrifugation. The culture supernatants were passed through a 0.2 micrometer filter, placed into a flask, and most of the water was allowed to evaporate. This led to the formation of crystals in the flasks. The remaining culture supernatants were discarded, and the crystals were redissolved in 10 milliliters of distilled water. The solutions were placed into a test tube, and most of the water was allowed to evaporate. This led to the formation of crystals in the test tubes. The supernatants were discarded, and the crystals were dissolved in 5 milliliters of distilled water. The resulting solutions were submitted to analysis, using the HPLC assay described in Example 5, and all were found to be composed of shikimic acid with a purity of greater than 99%.

Shikimic Acid Recovery
Laboratory Evaluation System

The following describes a laboratory evaluation system for aqueous process solutions comprising shikimic acid, inorganic monovalent salts, and glyphosate provided by the fermentation method and plant method.

For isolation of shikimic acid prepared by the fermentation method, a fermentation broth was centrifuged to remove cellular debris, followed by filtration through a Celite pad and a 0.2 μm filter. For isolation of shikimic acid prepared by the plant method, the solution utilized was prepared from soybean plants that were grown in a greenhouse for 21 days to approximately the V2 or V3 stage, after which the plants were then sprayed with ROUNDUP WEATHERMAX at 800 g/ha and harvested 3 days later. The stems and leaves of the plants were frozen on dry ice and stored at −80° C. for approximately 14 days until further processing. Plant extraction was conducted by grinding the stems and leaves into a powder and contacting the powder with 0.1 N aqueous HCl solution. The solution resulting from the plant extraction was isolated from the powder by centrifugation followed by filtration through a 0.2 μm filter. A Celite pad was not used for processing the plant extract.

Figure 8:
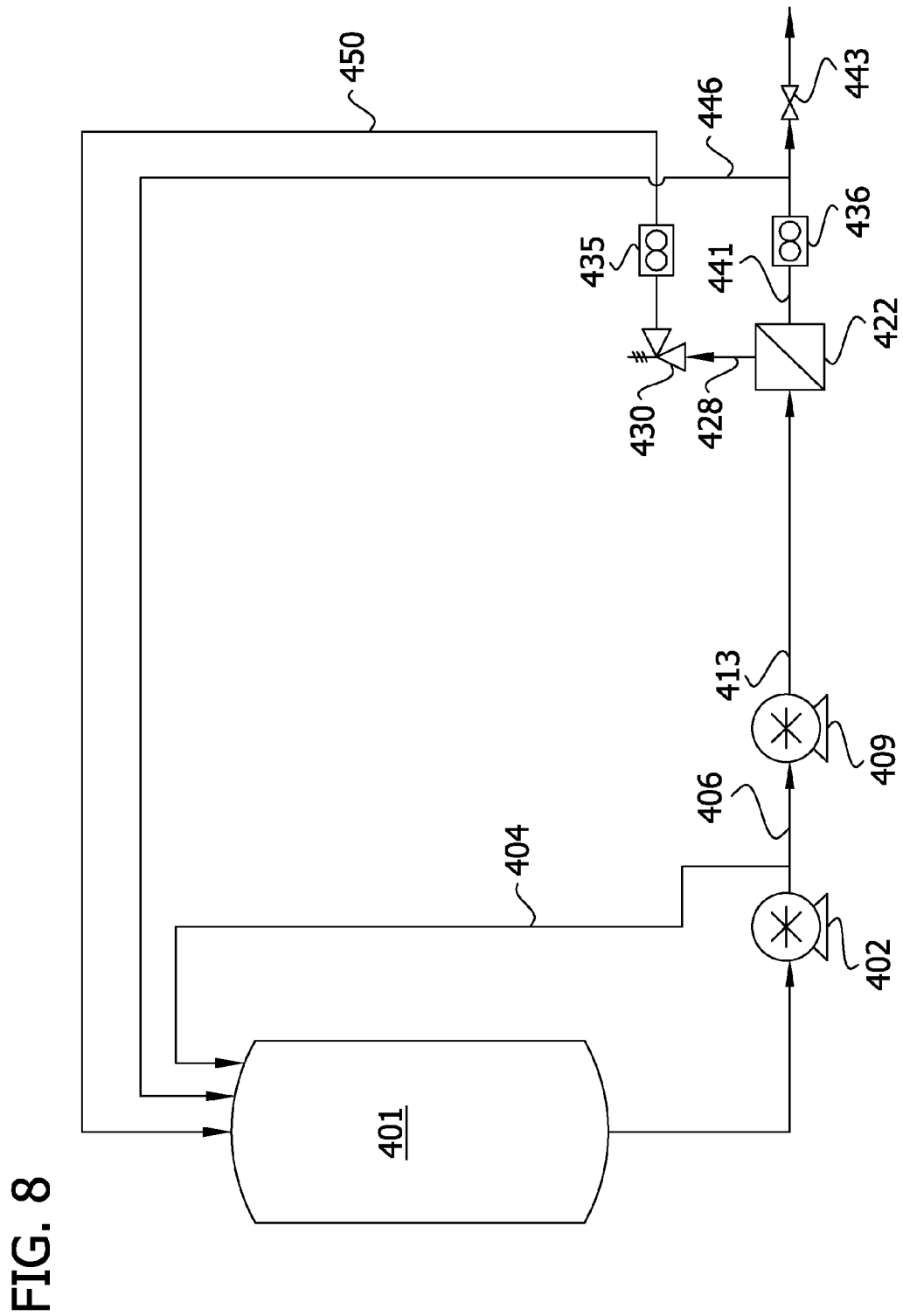
FIG. 8 is a flowsheet depicting a laboratory evaluation system.

Laboratory membrane separation experiments were conducted using a setup shown schematically in FIG. 8 that allowed for the processing of the shikimic acid solution resulting from the fermentation route and the shikimic acid solution resulting from the plant extraction route. The laboratory evaluation system included a shikimic acid solution feed vessel 401, two pumps 402 and 409, a membrane separation unit 422, and various process control equipment including valves, pressure indicators, and temperature controllers.

The first pump 402 was a small centrifugal pump that was used as a booster pump. Booster pump 402 served two purposes. Primarily, the booster pump provided a pressurized shikimic acid solution feed stream 406 for high pressure pump 409. The booster pump also recycled a portion 404 of the shikimic acid solution feed it removed from feed vessel 401 back to the feed vessel. This provided mixing of the contents of feed vessel 401. Feed vessel 401 was also equipped with an external jacket (not shown) that was used to keep the contents of the feed vessel at a given set point temperature.

Pressurized shikimic acid solution feed stream 406 from booster pump 402 was pressurized further by high pressure positive displacement pump 409 (Wanner diaphragm pump) that was capable of generating a feed stream flow of approximately 3.8 liters/min at 6996 kPa. A variable speed drive was installed on the pump drive to allow for feed flow rate control. High pressure pump 409 was used to send a highly pressurized shikimic acid solution feed stream 413 on to membrane separation unit 422.

Bench-scale spiral-wound membranes were tested in the laboratory evaluation system. The operating pressure was controlled by a throttle valve 430 positioned on the outlet from which retentate 428 was withdrawn from membrane separation unit 422. Operating pressures varied from about 1732 to about 4482 kPa absolute, while the target operating temperatures varied from about 15° C. to about 30° C.

In all laboratory membrane separation experiments, retentate 428 was recycled to feed vessel 401 after it exited the housing of membrane separation unit 422 in retentate recycle stream 450. The retentate passed through a flow meter 435 that provided for monitoring of the retentate flow rate. The permeate 441 exiting the housing of membrane separation unit 422 was also passed through a flow meter 436 that provided for monitoring of the permeate flow rate.

The permeate 441 could be diverted to a waste stream 443 or recycled to feed vessel 401 in permeate recycle stream 446 depending upon the type of experiment conducted. During a "recycle" experiment, the retentate and permeate were each recycled to feed vessel 401 along with the permeate retentate to provide a constant mother liquor feed composition throughout the experiment. This type of experiment was used to generate data regarding the stability of membrane flux and rejection characteristics. During a "batch concentration" experiment, the permeate would be diverted to waste, while the retentate was recycled to the feed vessel 401. This type of experiment allowed for the evaluation of membrane flux and rejection characteristics while the concentration of components, such as shikimic acid, inorganic salts, and glyphosate, in the shikimic acid solution feed was increasing.

High performance liquid chromatography (HPLC) and mass spectrometry were employed to analyze the process streams associated with the membrane separation experiments. Mass spectrometry was used to quantify the concentrations of shikimic acid and N-(phosphonomethyl)glycine. A Dionex AS11 anion exchange HPLC column using a 10 mM aqueous KOH solution as mobile phase was used to quantify the concentrations of monovalent and multivalent inorganic ions that include but are not limited to chloride, sulfate, ammonium, potassium, and phosphate anions.

A performance indicator known as solute rejection was calculated for each of the components of the shikimic acid feed solution using the data from the HPLC and mass spectrometry analysis. Solute rejection was defined as difference between one and the ratio of permeate concentration (Cp) for a component to the average of the process stream (Cs) and retentate concentration (Cr): $1 - Cp/((Cs+Cr)/2)$.

Example 12

Contacting Shikimic Acid with a Nanofiltration Membrane to Evaluate Membrane Rejection Characteristics as a Function of pH This example illustrates experiments conducted utilizing spiral-wound nanofiltration membranes to assess the impact of pH on membrane rejection characteristics for components in the shikimic acid feed solution.

The performance of a polyamide thin-film based nanofiltration membrane with a nominal molecular weight cut off (MWCO) of 250 daltons available from GE Osmonics was evaluated as pH of the shikimic acid feed solution varied from approximately 3.0 to approximately 5.0 by the addition of ammonium hydroxide. The shikimic acid feed solution flow rate was maintained at approximately 3.8 liters per minute, the operating temperature was maintained at about 18° C., and the operating pressure was maintained at about 3448 kPa. The concentration of shikimic acid in the shikimic acid feed solution was approximately 1.0% by weight. Five conditions were evaluated in a recycle-mode experiment using the Laboratory Evaluation System described above as the pH was incrementally increased from 3.1 to 5.0 in increments of approximately 0.5 pH units. Samples were collected at each condition once the process had stabilized for thirty minutes. The results are reported in Table 3.

TABLE 3

Experimental Testing to Assess Impact of pH on
Shikimic Acid Solution Purification by Contact with a GE
Osmonics Nanofiltration Membrane in Laboratory Evaluation System

| Approximate solution pH | Ratio of shikimic acid rejection to glyphosate rejection | Ratio of shikimic acid rejection to inorganic salt rejection | Ratio of shikimic acid rejection to phenylalanine rejection |
|---|---|---|---|
| 3.1 | 0.75 | 1.34 | 0.77 |
| 3.5 | 0.70 | 1.44 | 0.74 |
| 4.0 | 0.66 | 1.51 | 0.72 |
| 4.6 | 0.71 | 1.68 | 0.79 |
| 5.1 | 0.83 | 2.02 | 0.97 |

As shown in Table 3, shikimic acid can be most efficiently separated from glyphosate and phenylalanine at a pH of approximately 4.0. Also, it appears that the shikimic acid can be more efficiently separated from inorganic monovalent ions as pH is increased. Although the data in this Example were generated from an experiment utilizing a shikimic acid solution derived from the fermentation route, it is currently believed that membrane performance is similarly impacted by pH when contacting a shikimic acid solution provided by the plant extraction route.

Example 13

Purification of Plant Extraction Route-Based Shikimic Acid Solution by Contacting a Shikimic Acid Feed Solution Stream with a Nanofiltration Membrane This example illustrates experiments conducted utilizing spiral-wound nanofiltration membranes for the purification of a shikimic acid solution that was generated by the plant method.

A polyamide thin-film based nanofiltration membrane with a nominal molecular weight cut off (MWCO) of 250 daltons available from GE Osmonics was utilized in batch concentration mode to purify a shikimic acid solution that was generated from the plant route. The shikimic acid feed solution flow rate was maintained at approximately 3.8 liters per minute, the operating temperature varied from about 17° C. to about 22° C., the operating pressure was maintained at about 3448 kPa, and the shikimic acid feed solution pH was adjusted and maintained at about 4.0. The concentration of shikimic acid in the shikimic acid feed solution at the beginning of the experiment was approximately 0.1% by weight. Samples were collected as additional permeate was generated and removed from the system. The results are reported in Table 4.

TABLE 4

Purification of Plant-Extraction Route Shikimic Acid
Solution by Contact with a GE Osmonics Nanofiltration Membrane
in Laboratory Evaluation System

| Approximate amount of initial shikimic acid feed solution removed as permeate (%) | Concentration of shikimic acid in feed solution in wt % | Ratio of shikimic acid concentration to glyphosate concentration in feed solution | Estimated removal of inorganic monovalent ions (%) |
|---|---|---|---|
| 0 | 0.097 | 33 | 0 |
| 25 | 0.113 | 31 | 21 |
| 40 | 0.128 | 30 | 35 |

As can be seen in Table 4, a shikimic acid solution resulting from the plant extraction route may be purified by using nanofiltration membranes to sufficiently remove small inorganic monovalent ions and thus purify the shikimic acid solution, which may then be processed further in a separate unit operation, such as evaporation, to concentrate the shikimic acid.

All of the compositions and/or methods and/or processes and/or apparatus disclosed and claimed herein can be made and executed without undue experimentation in light of the instant disclosure. While the compositions and methods of this invention have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents that are chemically and/or physiologically related may be substituted for the agents described herein while the same or similar results would be achieved. All such similar substitutions and modifications apparent to those skilled in the art are deemed to be within the scope and concept of the invention. To the extent necessary to enable and describe the instant invention, all references cited are herein incorporated by reference.

REFERENCES

The following references, to the extent that they provide exemplary procedural or other details supplementary to those set forth herein, are specifically incorporated herein by reference.

Abrecht, S., P. Harrington, H. Iding, M. Karpf, R. Trussardi, B. Wirz, and U. Zutter. 2004. The synthetic development of the anti-influenza neuraminidase inhibitor oseltamivir phosphate (TAMIFLU): A challenge for synthesis and process research. Chimia 58: 621-629.

Adachi, O., Y. Ano, H. Toyama and K. Matsushita. 2006. High Shikimate Production from Quinate with Two Enzymatic Systems of Acetic Acid Bacteria. Biosci. Biotechnol. Biochem. (10): 2579-2582

Amrhein, N., B. Deus, P. Gehrke, and H. C. Steinrucken. 1980. The site of inhibition of the shikimate pathway by glyphosate. II. Interference of glyphosate with chorismate formation in vivo and in vitro. Plant Physiol. 66: 830-834.

Amrhein, N., D. Johanning, J. Schab, and A. Schulz. 1983. Biochemical basis for glyphosate-tolerance in a bacterium and a plant tissue culture. FEBS Letters 157: 191-196.

Anderson, K. A., W. T. Cobb, and B. R. Loper. 2001. Analytical method for determination of shikimic acid: Shikimic acid proportional to glyphosate application rates. Commun. Soil. Sci. Plant Anal. 32: 2831-2840.

Anderson, K. A. Method of Isolating Shikimic Acid From A Plant. International Publication No. WO 2008/027570 A2.

Armstrong, K. A., R. Acosta, E. Ledner, Y. Machida, M. Pancotto, M. McCormick, H. Ohtsubo, and E. Ohtsubo. 1984. A 37×103 molecular weight plasmid-encoded protein is required for replication and copy number control in the plasmid pSC101 and its temperature-sensitive derivative pHS1. J. Mol. Biol. 175: 331-347.

Ausubel, F. M., R. Brent, R. E. Kingston, D. D. Moore, J. G. Seidman, J. A. Smith, and K. Struhl. 2005. "Current protocols in molecular biology". John Wiley and Sons, New York.

Baird, D. D., R. P. Upchurch, W. B. Homesley, and J. E. Franz. 1971. Introduction of a new broadspectrum postemergence herbicide class with utility of herbaceous perennial weed control. Proc. North Central Weed Control Conf. 26: 64-68.

Balbas, P., X. Soberon, E. Merino, M. Zurita, H. Lomeli, F. Valle, N. Flores and F. Bolivar. 1986. Plasmid vector pBR322 and its special-purpose derivatives—a review. Gene 50: 3-40.

Balbas, P., X. Soberon, F. Bolivar, and R. L. Rodriguez. 1988. The plasmid pBR322. In Rodriguez, R. L., and D. T. Denhardt (ed.) "Vectors. A survey of molecular cloning vectors and their uses", pp 5-41. Butterworths, Boston, Mass.

Bentley, W. E., N. Mirjalili, D. C. Andersen, R. H. Davis and D. S. Kompala. 1990. Plasmid-encoded protein: the principal factor in the "metabolic burden" associated with recombinant bacteria. Biotech. and Bioeng. 35: 668-681.

Bischofberger, N. W., C. U. Kim, W. Lew, H. Liu, and M. A. Williams. Carbocyclic compounds. U.S. Pat. No. 5,763,483.

Bischofberger, N. W., C. U. Kim, W. Lew, H. Liu, and M. A. Williams. Compounds and methods for synthesis and therapy. U.S. Pat. No. 5,952,375.

Bischofberger, N. W., C. U. Kim, W. Lew, H. Liu, and M. A. Williams. Novel selective inhibitors of viral or bacterial neuraminidases. European Patent EP 0759917 B1.

Bischofberger, N. W., C. U. Kim, W. Lew, H. Liu, and M. A. Williams. Selective inhibitors of viral or bacterial neuraminidases. European Patent EP 0976734 B1.

Bogosian, G., J. P. O'Neil, and H. Q. Smith. Hybrid portable origin of replication plasmids. International Publication No. WO 2007/035323 A1.

Bolivar, F., R. L. Rodriguez, P. J. Greene, M. C. Betlach, H. L. Heyneker and H. W. Boyer. 1977. Construction and characterization of new cloning vehicles. II. A multipurpose cloning system. Gene 2: 95-113.

Bongaerts, J., M. Kramer, U. Muller, L. Raeven, and M. Wubbolts. 2001. Metabolic engineering for microbial production of aromatic amino acids and derived compounds. Metabolic Engineering 3: 289-300.

Bornemann, S., M. J. Ramjee, S. Balasubramanian, C. Abell, J. R. Coggins, D. J. Lowe, and R. N. F. Thorneley. 1995. *Escherichia coli* chorismate synthase catalyzes the conversion of (6S)-6-fluoro-5-enolpyruvylshikimate-3-phosphate to 6-fluorochorismate. Implications for the enzyme mechanism and the antimicrobial action of (6S)-6-fluoroshikimate. J. Biol. Chem. 270: 22811-22815.

Bradley, D. 2005. Star role for bacteria in controlling flu epidemic? Nature Reviews Drug Discovery 4: 945-946.

Brown, K. A., E. P. Carpenter, K. A. Watson, J. R. Coggins, A. R. Hawkins, M. H. J. Koch, and D. I. Svergun. 2003. Twists and turns: A tale of two shikimate-pathway enzymes. Biochem. Soc. Trans. 31: 543-547.

Buehring, N. W., J. H. Massey, and D. B. Reynolds. 2007. Shikimic acid accumulation in field-grown corn (*Zea mays*) following stimulated glyphosate drift. J. Agric. Food Chem. 55: 819-824.

Casali, N., and A. Preston. 2003. "E. coli plasmid vectors. Methods and applications". Humana Press, Totowa, N.J.

Chandran, S. S., J. Yi, K. M. Draths, R. von Daeniken, W. Weber, and J. W. Frost. 2003. Phosphoenolpyruvate availability and the biosynthesis of shikimic acid. Biotechnol. Prog. 19: 808-814.

Cleophax, J., D. Mercier and S. D. Gero. 1971. Stereospecific conversion of (−)-methyl tri-O-benzoylquinate to the corresponding (−)-methyl shikimate. Angew. Chem. Int. Ed. Engl. 10: 652-3

Cleophax, J., J. Leboul, D. Mercier, A. Gaudemer and S. D. Gero. 1971. Easy route to shikimic and 4-epishikimic acid derivatives. Bull. Soc. Chim. Fr. 2992-2995

Conn, E. E. 1986. "The shikimic acid pathway". (Volume 20 in the series "Recent advances in phytochemistry"). Plenum Press, New York.

Dangschat, G. and H. O. L Fischer. 1938. Conversion of quinic acid into shikimic acid. Naturwissenschaften 26: 562-5633

Dangschat, G. and H. O. L Fischer. 1950. Configurational relations between naturally occurring cyclic plant acids and glucose-transformation of quinic acid into shikimic acid. Biochim. Biophys. Acta 4: 199-204

Davies, G. M., K. J. Barrett-Bee, D. A. Jude, M. Lehan, W. W. Nichols, P. E. Pinder, J. L. Thain, W. J. Watkins, and R. G. Wilson. 1994. (6S)-6-fluoroshikimic acid, an antibacterial agent acting on the aromatic biosynthetic pathway. Antimicrob. Agents Chemother. 38: 403-406.

Davis, B. D., and E. S. Mingioli. 1953. Aromatic biosynthesis. VII. Accumulation of two derivatives of shikimic acid by bacterial mutants. J. Bacteriol. 66: 129-136.

De Clercq, E. 2002. Strategies in the design of antiviral drugs. Nature Reviews/Drug Discovery 1: 13-25.

Dell, K. A., and J. W. Frost. 1993. Identification and removal of impediments to biocatalytic synthesis of aromatics from D-glucose: Rate-limiting enzymes in the common aromatic pathway of aromatic amino acid biosynthesis. J. Am. Chem. Soc. 115: 11581-11589.

Falck, J. R., and P. Yadagiri. 1989. Enantiospecific synthesis of D-myo-inositol 1,4,5-trisphosphate from (−)-quinic acid. J. Org. Chem. 54: 5851-5852

Farina, V., and J. D. Brown. 2006. TAMIFLU: The supply problem. Angew. Chem. Int. Ed. 45: 7330-7334.

Federspiel, M., R. Fischer, M. Hennig, H.-J. Mair, T. Oberhauser, G. Rimmler, T. Albiez, J. Bruhin, H. Estermann, C. Gandert, V. Gockel, S. Gotzo, U. Hoffmann, G. Huber, G. Janatsch, S. Lauper, O. Rockel-Stabler, R. Trussardi, and A. G. Zwahlen. 1999. Industrial synthesis of the key precursor in the synthesis of the anti-influenza drug oseltamivir phosphate (Ro 64-0796/002, GS-4104-02): Ethyl (3R,4S,5S)-4,5-epoxy-3-(1-ethyl-propoxy)-cyclohex-1-ene-1-carboxylate. Organic Process Research and Development 3: 266-274.

Fischer, R. S., A. Berry, C. G. Gaines, and R. A. Jensen. 1986. Comparative action of glyphosate as a trigger of energy drain in eubacteria. J. Bacteriol. 168: 1147-1154.

Fotheringham, I. G., and J. Nelms. DNA encoding pheA feedback inhibition resistant enzyme analogs. U.S. Pat. No. 5,120,837.

Fotheringham, I. G., and J. Nelms. Methods and materials for pheA feedback inhibition resistance. European Patent 0418840 B1.

Franz, J. E., M. K. Mao, and J. A. Sikorski. 1997. "Glyphosate. A unique global herbicide". American Chemical Society Monograph 189. American Chemical Society, Washington, D.C.

Frost, J. W. Enhanced production of common aromatic pathway compounds. U.S. Pat. No. 5,168,056

Frost, J. W., K. M. Frost, and D. R. Knop. Biocatalytic synthesis of shikimic acid. International Publication No. WO 00/44923.

Frost, J. W., K. M. Frost, and D. R. Knop. Biocatalytic synthesis of shikimic acid. International Publication No. WO 02/29078.

Frost, J. W., K. M. Frost, and D. R. Knop. Biocatalytic synthesis of shikimic acid. U.S. Pat. No. 6,472,169.

Frost, J. W., K. M. Frost, and D. R. Knop. Biocatalytic synthesis of shikimic acid. U.S. Pat. No. 6,613,552.

Frost, J. W., K. D. Snell, and K. M. Frost. Deblocking the common pathway of aromatic amino acid synthesis. U.S. Pat. No. 5,776,736.

Frost, J. W., K. D. Snell, and K. M. Frost. Deblocking the common pathway of aromatic amino acid synthesis. European Patent EP 0763127 B1.

Fukuta, Y., T. Mita, N. Fukuda, M. Kanai, and M. Shibasaki. 2006. De novo synthesis of TAMIFLU via a catalytic asymmetric ring-opening of meso-aziridines with TMSN3. J. Am. Chem. Soc. 128: 6312-6313.

Garner, C., and K. M. Herrmann. 1983. Biosynthesis of phenylalanine. In Herrmann, K. M., and R. L. Somerville (ed.) "Amino acids: Biosynthesis and genetic regulation" pp. 323-338. Addison-Wesley Publishing Co., Reading, Mass.

Grossbard, E., and D. Atkinson. 1985. "The herbicide glyphosate". Butterworths, London.

Harring, T., J. C. Streibig, and S. Husted. 1998. Accumulation of shikimic acid: A technique for screening glyphosate efficacy. J. Agric. Food Chem. 46: 4406-4412.

Haslam, E. 1974. "The shikimate pathway". John Wiley and Sons, New York.

Haslam, E. 1993. "Shikimic acid. Metabolism and metabolites." John Wiley and Sons, Chichester, England.

Hasunuma, K., and M. Sekiguchi. 1977. Replication of plasmid pSC101 in Escherichia coli K12: Requirement for dnaA function. Molec. Gen. Genet. 154: 225-230.

Henry, W. B., D. L. Shaner, and M. S. West. 2007. Shikimate accumulation in sunflower, wheat, and proso millet after glyphosate application. Weed Science 55: 1-5.

Herrmann, K. M. 1983. The common aromatic biosynthetic pathway. In Herrmann, K. M., and R. L. Somerville (ed.) "Amino acids: Biosynthesis and genetic regulation" pp. 301-322. Addison-Wesley Publishing Co., Reading, Mass.

Herrmann, K. M. 1995a. The shikimate pathway: Early steps in the biosynthesis of aromatic compounds. The Plant Cell 7: 907-919.

Herrmann, K. M. 1995b. The shikimate pathway as an entry to aromatic secondary metabolism. Plant Physiol. 107: 7-12.

Herrmann, K. M., and L. M. Weaver. 1999. The shikimate pathway. Ann. Rev. Plant. Physiol. Plant Mol. Biol. 50: 473-503.

Ikeda, M. 2003. Amino acid production processes. In Faurie, R., and J. Thommel (ed.) "Vol. 79 in Advances in biochemical engineering biotechnology. Microbial production of amino acids." pp. 1-35. Springer-Verlag, Berlin.

Iomantas, Y. A. V., E. G. Abalakina, B. M. Polanuer, T. A. Yampolskaya, T. A. Bachina, and Y. I. Kozlov. Method for producing shikimic acid. U.S. Pat. No. 6,436,664.

Johansson, L. 2006. Metabolic analysis of shikimic acid producing Escherichia coli. PhD thesis, Lund University, Sweden.

Johansson, L., and G. Liden. 2006. Transcriptome analysis of a shikimic acid producing strain of Escherichia coli W3110 grown under carbon- and phosphate-limited conditions. J. Biotechnol. 126: 528-545.

Johansson, L., A. Lindskog, G. Silfversparre, C. Cimander, K. F. Nielsen, and G. Liden. 2005. Shikimic acid production by a modified strain of E. coli (W3110.shik1) under phosphate-limited and carbon-limited conditions. Biotechnol. Bioeng. 92: 541-552.

Khudyakov, Y. E., and H. A. Fields. 2003. "Artificial DNA: Methods and applications". CRC Press, Boca Raton, Fla.

Kim, C. U., W. Lew, M. A. Williams, H. Liu, L. Zhang, S. Swaminathan, N. Bischofberger, M. S. Chen, D. B. Mendel, C. Y. Tai, W. G. Layer, and R. C. Stevens. 1997. Influenza neuraminidase inhibitors possessing a novel hydrophobic interaction in the enzyme active site: Design, synthesis, and structural analysis of carbocyclic sialic acid analogues with potent anti-influenza activity. J. Am. Chem. Soc. 119: 681-690.

Kim, C. U., W. Lew, M. A. Williams, H. Wu, L. Zhang, X. Chen, P. A. Escarpe, D. B. Mendel, W. G. Layer, and R. C. Stevens. 1998. Structure-activity relationship studies of novel carbocyclic influenza neuraminidase inhibitors. J. Am. Chem. Soc. 41: 2451-2460.

Knop, D. R., K. M. Draths, S. S. Chandran, J. L. Barker, R. von Daeniken, W. Weber, and J. W. Frost. 2001. Hydroaromatic equilibration during biosynthesis of shikimic acid. J. Am. Chem. Soc. 123: 10173-10182.

Kramer, M., J. Bongaerts, R. Bovenberg, S. Kremer, U. Muller, S. Orf, M. Wubbolts, and L. Raeven. 2003. Metabolic engineering for microbial production of shikimic acid. Metabolic Engineering 5: 277-283.

Lew, W., C. U. Kim, H. Liu, and M. A. Williams. Carbocyclic compounds. U.S. Pat. No. 5,866,601.

Malmberg, M., and B. Westrup. Process for the isolation of polyhydroxy cyclic carboxylic acids. U.S. Pat. No. 6,794,164.

McConkey, G. A. 1999. Targeting the shikimate pathway in the malaria parasite Plasmodium falciparum. Antimicrob. Agents Chemother. 43: 175-177.

Mueller, T. C., J. H. Massey, R. M. Hayes, C. L. Main, and C. N. Stewart. 2003. Shikimate accumulates in both glyphosate-sensitive and glyphosate-resistant horseweed (Conyza canadensis L. Cronq.). J. Agric. Food Chem. 51: 680-684.

Nelms, J., R. M. Edwards, J. Warwick, and I. Fotheringham. 1992. Novel mutations in the pheA gene of Escherichia coli K-12 which result in highly feedback inhibition-resistant variants of chorismate mutase/prephenate dehydrogenase. Appl. Environ. Microbiol. 58: 2592-2598.

Payne, R., and M. Edmonds. 2005. Isolation of shikimic acid from star aniseed. J. Chem. Ed. 82: 599-600.

Pittard, A. J. 1987. Biosynthesis of the aromatic amino acids, p. 368-394. In Neidhardt, F. C., J. L. Ingraham, K. B. Low, B. Magasanik, M. Schaechter, and H. E. Umbarger (ed.) "Escherichia coli and Salmonella: Cellular and molecular biology". American Society for Microbiology Press, Washington, D.C.

Pittard, A. J. 1996. Biosynthesis of the aromatic amino acids, p. 458-484. In Neidhardt, F. C., R. Curtiss, J. L. Ingraham, E. C. C. Lin, K. B. Low, B. Magasanik, W. S. Reznikoff, M. Riley, M. Schaechter, and H. E. Umbarger (ed.) "Escherichia coli and Salmonella: Cellular and molecular biology". American Society for Microbiology Press, Washington, D.C.

Pline, W. A., J. W. Wilcut, S. O. Duke, K. L. Edmisten, and R. Wells. 2002. Tolerance and accumulation of shikimic acid in response to glyphosate applications in glyphosate-resistant and nonglyphosate-resistant cotton (Gossypium hirsutum L.). J. Agric. Food Chem. 50: 506-512.

Polen, T., M. Kramer, J. Bongaerts, M. Wubbolts, and V. F. Wendisch. 2005. The global gene expression response of Escherichia coli to L-phenylalanine. J. Biotechnol. 115: 221-237.

Pouwels, P. H., B. E. Enger-Valk, and W. J. Brammar. 1985. "Cloning vectors. A laboratory manual". Elsevier Science Publishers, Amsterdam.

Rao, A. V. R., T. K. Chakraborty, D. Sankaranayanan, and A. V. Purandare. 1991. Studies directed towards the synthesis of immunosuppressive agent FK-506: Synthesis of the entire top-half. Tetrahedron Lett. 32: 547-550

Roberts, F., C. W. Roberts, J. J. Johnson, D. E. Kyle, T. Krell, J. R. Coggins, G. H. Coombs, W. K. Milhous, S. Tzipori, D.

J. P. Ferguson, D. Chakrabarti, and R. McLeod. 1998. Evidence for the shikimate pathway in apicomplexan parasites. Nature 393: 801-805.

Roberts, C. W., F. Roberts, R. E. Lyons, M. J. Kiristis, E. J. Mui, J. Finnerty, J. J. Johnson, D. J. P. Ferguson, J. R. Coggins, T. Krell, G. H. Coombs, W. K. Milhous, D. E. Kyle, S. Tzipori, J. Barnwell, J. B. Dame, J. Carlton, and R. McLeod. 2002. The shikimate pathway and its branches in apicomplexan parasites. J. Infect. Dis. 185 (Suppl. 1): S25-36.

Rodriguez, R. L., and D. T. Denhardt. 1988. "Vectors. A survey of molecular cloning vectors and their uses". Butterworths, Boston, Mass.

Rohloff, J. C., K. M. Kent, M. J. Postich, M. W. Becker, H. H. Chapman, D. E. Kelly, W. Lew, M. S. Louie, L. R. McGee, E. J. Prisbe, L. M. Schultze, R. H. Yu, and L. Zhang. 1998. Practical total synthesis of the anti-influenza drug GS-4104. J. Org. Chem. 63: 4545-4550.

Sadaka, M., and A. Garcia. 1999. Extraction of shikimic and quinic acids. Chem. Eng. Commun. 173: 91-102.

Sambrook, J., and D. W. Russell. 2001. "Molecular cloning. A laboratory manual". Third Edition. Cold Spring Harbor Laboratory Press, Cold Spring Harbor, N.Y.

Shirai, M., R. Miyata, S. Sasaki, K. Sakamoto, S. Yahanda, K. Shibayama, T. Yonehara, and K. Ogawa. Microorganism belonging to the genus *Citrobacter* and process for producing shikimic acid. European Patent Application EP 1092766 A1.

Sprenger, G., R. Siewe, H. Sahm, M. Karutz, and T. Sonke. Microbial preparation of substances from aromatic metabolism. U.S. Pat. No. 6,316,232.

Starcevic, A., S. Akthar, W. C. Dunlap, J. M. Shick, D. Hranueli, J. Cullum, and P. F. Long. 2008. Enzymes of the shikimic acid pathway encoded in the genome of a basal metazoan, *Nematostella vectensis*, have microbial origins. Proc. Natl. Acad. Sci. 105: 2533-2537.

Steinrucken, H. C., and N. Amrhein. 1980. The herbicide glyphosate is a potent inhibitor of 5-enolpyruvyl-shikimic acid-3-phosphate synthase. Biochem. Biophys. Res. Commun. 94: 1207-1212.

Steinrucken, H. C., and N. Amrhein. 1984. 5-enolpyruvylshikimate-3-phosphate synthase of *Klebsiella pneumoniae*. 2. Inhibition by glyphosate [N-(phosphonomethyl) glycine]. Eur. J. Biochem. 143: 351-357.

Stryer, L. 1995. "Biochemistry" Fourth Edition. W.H. Freeman and Company, New York.

Tan, D. S., M. A. Foley, B. R. Stockwell, M. D. Shair, and S. L. Schreiber. 1999. Synthesis and preliminary evaluation of a library of polycyclic small molecules for use in chemical genetic assays. J. Am. Chem. Soc. 121: 9073-9087.

Van der Does, T., J. Booij, E. E. Kers, E. J. A. M. Leenderts, M. Sibeijn, and V. Agayn. Process for the recovery of shikimic acid. International Publication No. WO 02/06203.

Vogel, H. J., and D. M. Bonner. 1956. Acetylornithinase of *Escherichia coli*: Partial purification and some properties. J. Biol. Chem. 218: 97-106.

Wanner, B. L. 1996. Phosphorus assimilation and control of the phosphate regulon, p. 1357-1381. In Neidhardt, F. C., R. Curtiss, J. L. Ingraham, E. C. C. Lin, K. B. Low, B. Magasanik, W. S. Reznikoff, M. Riley, M. Schaechter, and H. E. Umbarger (ed.) "*Escherichia coli* and *Salmonella*: Cellular and molecular biology". American Society for Microbiology Press, Washington, D.C.

Weiss, U., and J. M. Edwards. 1980. "The biosynthesis of aromatic compounds". John Wiley and Sons, New York.

White, J. D., J. H. Cammack, and K. Sakuma. 1989. The synthesis and absolute configuration of mycosporins. A novel application of the Staudinger reaction. J. Am. Chem. Soc. 111: 8970-8972

Yeung, Y.-Y., S. Hong, and E. J. Corey. 2006. A short enantioselective pathway for the synthesis of the anti-influenza neuraminidase inhibitor oseltamivir from 1,3-butadiene and acrylic acid. J. Am. Chem. Soc. 128: 6310-6311.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above without departing from the scope of the invention, it is intended that all matter contained in the above description and shown in the accompanying drawings shall be interpreted as illustrative and not in a limiting sense.

What is claimed is:

1. A process for recovery of shikimic acid from an aqueous process stream further comprising glyphosate, the process comprising:

introducing the aqueous process stream into a membrane separation unit comprising at least one separation membrane; and contacting the aqueous process stream and the at least one separation membrane to form a retentate and a permeate.

2. The process as set forth in claim 1 wherein the at least one separation membrane is selective to produce a retentate enriched in shikimic acid relative to the permeate.

3. The process as set forth in claim 2 wherein the at least one separation membrane is selective to produce a retentate enriched in glyphosate relative to the permeate.

4. The process as set forth in claim 2 wherein the retentate comprises shikimic acid and glyphosate and the process further comprises separating shikimic acid from glyphosate in the retentate.

5. The process as set forth in claim 4 wherein said separating comprises introducing the retentate into at least one ion exchange zone and contacting the retentate with an ion exchange resin contained therein and selective for removal of glyphosate therefrom to form an aqueous product solution comprising shikimic acid and depleted in glyphosate relative to the retentate.

6. The process as set forth in claim 2 further comprising diluting the aqueous process stream during contact with the at least one separation membrane such that the membrane separation unit operates as a diafiltration membrane separation unit.

7. The process as set forth in claim 2 wherein the membrane separation unit comprises a plurality of separation membranes, the plurality of membranes comprising a first separation membrane and a second separation membrane, the process further comprising:

(a) introducing the retentate from the first separation membrane into the aqueous process stream;

(b) contacting the permeate from the first separation membrane with the second separation membrane to form a second retentate and a second permeate, wherein the second retentate is enriched in shikimic acid relative to the second permeate; and (c) introducing the second retentate into the aqueous process stream.

8. The process as set forth in claim 7 wherein the plurality of separation membranes further comprises a third separation membrane, the process further comprising:
(d) contacting the second permeate with the third separation membrane to form a third retentate and a third permeate, wherein the third retentate is enriched in shikimic acid relative to the third permeate; and
(e) introducing the third retentate into the aqueous process stream.

9. The process as set forth in claim 8 wherein one or more of steps (a) through (e) are conducted substantially continuously.

10. The process as set forth in claim 1 wherein the at least one separation membrane is selective to produce a permeate enriched in shikimic acid relative to the retentate.

11. The process as set forth in claim 10 wherein the at least one separation membrane is selective to produce a permeate depleted in glyphosate relative to the retentate.

12. The process as set forth in claim 10 wherein the aqueous process stream comprises a fermentation broth prepared by a process comprising:
a) providing a microorganism culture, wherein the microorganism is capable of synthesizing shikimate-3-phosphate; and
b) contacting the microorganism with glyphosate.

13. The process as set forth in claim 10 wherein the permeate comprises shikimic acid and phenylalanine and the process further comprises separating shikimic acid from phenylalanine in the permeate.

14. The process as set forth in claim 13 wherein said separating comprises introducing the permeate into at least one ion exchange zone and contacting the permeate with an ion exchange resin contained therein and selective for removal of phenylalanine therefrom to form an aqueous product solution comprising shikimic acid and depleted in phenylalanine relative to the permeate.

15. The process as set forth in claim 13 further comprising diluting the aqueous process stream during contact with the at least one separation membrane such that the membrane separation unit operates as a diafiltration membrane separation unit.

16. The process as set forth in claim 10 wherein the membrane separation unit comprises a plurality of separation membranes, the plurality of membranes comprising a first separation membrane and a second separation membrane, the process further comprising:
(a) introducing the permeate from the first separation membrane into the aqueous process stream;
(b) contacting the retentate from the first separation membrane with the second separation membrane to form a second retentate and a second permeate, wherein the second permeate is enriched in shikimic acid relative to the second retentate; and
(c) introducing the second permeate into the aqueous process stream.

17. The process as set forth in claim 16 wherein the plurality of separation membranes further comprises a third separation membrane, the process further comprising:
(d) contacting the second retentate with the third separation membrane to form a third retentate and a third permeate, wherein the third permeate is enriched in shikimic acid relative to the third permeate; and
(e) introducing the third permeate into the aqueous process stream.

18. The process as set forth in claim 17 wherein one or more of steps (a) through (e) are conducted substantially continuously.

19. The process as set forth in claim 4 wherein separating shikimic acid from glyphosate in the retentate forms an aqueous product solution comprising shikimic acid and depleted in glyphosate relative to the retentate.

20. The process as set forth in claim 13 wherein separating shikimic acid from phenylalanine in the permeate forms an aqueous product solution comprising shikimic acid and depleted in phenylalanine relative to the permeate.

* * * * *